United States Patent
Luo et al.

(10) Patent No.: US 9,663,822 B2
(45) Date of Patent: *May 30, 2017

(54) MULTIPLEX CAPTURE OF NUCLEIC ACIDS

(71) Applicant: Affymetrix, Inc., Santa Clara, CA (US)

(72) Inventors: Yuling Luo, San Ramon, CA (US); Yunqing Ma, San Jose, CA (US); Gary McMaster, Ann Arbor, MI (US); Quan Ngoc Nguyen, San Ramon, CA (US); Frank Witney, Oakland, CA (US); Wen Yang, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 14/105,080

(22) Filed: Dec. 12, 2013

(65) Prior Publication Data

US 2014/0194296 A1 Jul. 10, 2014

Related U.S. Application Data

(63) Continuation of application No. 12/930,041, filed on Dec. 23, 2010, now Pat. No. 8,632,970, which is a continuation-in-part of application No. 11/431,092, filed on May 8, 2006, now Pat. No. 8,628,918.

(60) Provisional application No. 60/679,500, filed on May 9, 2005.

(51) Int. Cl.
C12Q 1/68 (2006.01)
C12M 1/34 (2006.01)
C12P 19/34 (2006.01)
C07H 21/04 (2006.01)

(52) U.S. Cl.
CPC ......... *C12Q 1/6874* (2013.01); *C12Q 1/6832* (2013.01); *C12Q 1/6834* (2013.01); *C12Q 1/6837* (2013.01)

(58) Field of Classification Search
None
See application file for complete search history.

(56) References Cited

U.S. PATENT DOCUMENTS

| | | |
|---|---|---|
| 4,868,105 A | 9/1989 | Urdea et al. |
| 5,093,232 A | 3/1992 | Urdea et al. |
| 5,122,599 A | 6/1992 | Barnett et al. |
| 5,124,246 A | 6/1992 | Urdea et al. |
| 5,185,244 A | 2/1993 | Wallace |
| 5,198,357 A | 3/1993 | Holmovist et al. |
| 5,284,940 A | 2/1994 | Lin et al. |
| 5,334,499 A | 8/1994 | Burdick et al. |
| 5,374,524 A | 12/1994 | Miller |
| 5,393,672 A | 2/1995 | Ness et al. |
| 5,436,327 A | 7/1995 | Southern et al. |
| 5,543,305 A | 8/1996 | Cummins et al. |
| 5,606,045 A | 2/1997 | Dandliker et al. |
| 5,633,134 A | 5/1997 | Shuber |
| 5,635,352 A | 6/1997 | Urdea et al. |
| 5,681,697 A | 10/1997 | Urdea et al. |
| 5,681,702 A | 10/1997 | Collins et al. |
| 5,700,637 A | 12/1997 | Southern |
| 5,747,244 A | 5/1998 | Sheridan et al. |
| 5,780,227 A | 7/1998 | Sheridan et al. |
| 5,804,684 A | 9/1998 | Su |
| 5,849,481 A | 12/1998 | Urdea et al. |
| 5,888,778 A | 3/1999 | Shuber |
| 5,945,515 A | 8/1999 | Chomczynski |
| 6,007,994 A | 12/1999 | Ward et al. |
| 6,221,589 B1 | 4/2001 | Lane et al. |
| 6,268,147 B1 | 7/2001 | Beattie et al. |
| 6,306,643 B1 | 10/2001 | Gentalen et al. |
| 6,352,827 B1 | 3/2002 | Lin et al. |
| 6,418,382 B2 | 7/2002 | Rothberg et al. |
| 6,428,957 B1 | 8/2002 | Delenstarr |
| 6,472,187 B1 | 10/2002 | Tonoike et al. |
| 6,562,575 B1 | 5/2003 | Dahl |
| 6,610,475 B1 | 8/2003 | Kacian et al. |
| 6,670,461 B1 | 12/2003 | Nielsen et al. |
| 6,670,464 B1 | 12/2003 | Shimkets et al. |
| 6,673,914 B1 | 1/2004 | Hoon |
| 6,794,499 B2 | 9/2004 | Wengel et al. |
| 6,852,490 B2 | 2/2005 | Gentalen et al. |
| 7,034,133 B2 | 4/2006 | Wengel et al. |
| 7,399,846 B2 | 7/2008 | Southern et al. |

(Continued)

FOREIGN PATENT DOCUMENTS

| | | |
|---|---|---|
| EP | 1 428 892 A1 | 6/2004 |
| WO | WO 94/00598 A1 | 1/1994 |

(Continued)

OTHER PUBLICATIONS

U.S. Appl. No. 11/521,115.
Affymetrix "QuantiGene Plex 2.0 Assay" User Manual, 2010, 46 pages.
Aitken (1999) "Protein consensus sequence motifs," Mol Biotechnol. 12(3):241-253.
Albert et al. (2007) "Direct selection of human genomic loci by microarray hybridization," Nature Methods, 4(11):903-905.
Al-Soud et al. (1998) "A sample preparation method which facilitates detection of bacteria in blood cultures by the polymerase chain reaction," *J. Microbiol. Meth.*, 32:217-224.
Application Note from Amersham Biosciences, "Whole genome amplification from crude blood lysates," 2003 (4 pages).
Application Note from Applied Biosystems, "Total RNA purification from whole blood," 2002 (6 pages).
Bach et al. (1999) "Magnetic capture-hybridization method for purification and probing of mRNA for neutral protease of *Bacillus cereus*," *Journal of Microbiological Methods*, 37:187-192.

(Continued)

*Primary Examiner* — Sarae Bausch
(74) *Attorney, Agent, or Firm* — Quine Intellectual Property Law Group, P.C.

(57) ABSTRACT

Methods of capturing two or more nucleic acids simultaneously from a single sample are provided. Different nucleic acids are captured through cooperative hybridization events on different subsets of particles or at different selected positions on a spatially addressable solid support. Methods of capturing one or more long nucleic acids and methods of capturing one or more nucleic acid for sequencing are also provided. Compositions, kits, and systems related to the methods are also described.

25 Claims, 9 Drawing Sheets

(56) References Cited

U.S. PATENT DOCUMENTS

| | | |
|---|---|---|
| 7,572,582 B2 | 8/2009 | Wengel et al. |
| 7,745,091 B2 | 6/2010 | True |
| 7,745,092 B2 | 6/2010 | True |
| 7,803,541 B2 | 9/2010 | Luo et al. |
| 7,927,798 B2 | 4/2011 | Zheng et al. |
| 7,955,794 B2 * | 6/2011 | Shen et al. .................. 435/6.11 |
| 2002/0034753 A1 | 3/2002 | Yang et al. |
| 2002/0034754 A1 | 3/2002 | Reed et al. |
| 2002/0106644 A1 | 8/2002 | Rosenow |
| 2002/0172953 A1 | 11/2002 | Mirkin et al. |
| 2002/0187470 A1 | 12/2002 | Casey et al. |
| 2003/0059803 A1 | 3/2003 | Werner et al. |
| 2003/0165935 A1 | 9/2003 | Vann |
| 2003/0211489 A1 | 11/2003 | Shen et al. |
| 2004/0023248 A1 | 2/2004 | O'Malley |
| 2004/0072231 A1 | 4/2004 | Mirkin et al. |
| 2004/0076954 A1 | 4/2004 | Caldwell et al. |
| 2004/0086930 A1 | 5/2004 | Tereba et al. |
| 2004/0115686 A1 | 6/2004 | Dolginow et al. |
| 2004/0248103 A1 | 12/2004 | Feaver et al. |
| 2005/0009063 A1 | 1/2005 | Xia et al. |
| 2005/0019842 A1 | 1/2005 | Prober et al. |
| 2005/0170370 A1 | 8/2005 | Rabbani et al. |
| 2005/0282220 A1 | 12/2005 | Prober et al. |
| 2006/0068417 A1 * | 3/2006 | Becker ................. C12Q 1/6834 435/6.12 |
| 2006/0172284 A1 | 8/2006 | Zheng et al. |
| 2006/0263769 A1 | 11/2006 | Luo et al. |
| 2006/0286583 A1 | 12/2006 | Luo et al. |
| 2007/0015188 A1 | 1/2007 | Luo et al. |
| 2007/0161015 A1 | 7/2007 | Zheng et al. |
| 2007/0161020 A1 | 7/2007 | Luo et al. |
| 2008/0038725 A1 | 2/2008 | Luo et al. |
| 2008/0050746 A1 | 2/2008 | McMaster et al. |
| 2008/0176242 A1 | 7/2008 | McMaster et al. |
| 2008/0220979 A1 | 9/2008 | Wang et al. |
| 2009/0081688 A1 | 3/2009 | Luo et al. |
| 2009/0131269 A1 | 5/2009 | Martin et al. |
| 2009/0149340 A1 | 6/2009 | True |
| 2009/0170060 A1 | 7/2009 | Kermekchiev et al. |
| 2010/0227279 A1 | 9/2010 | True |
| 2010/0227770 A1 | 9/2010 | True |

FOREIGN PATENT DOCUMENTS

| | | |
|---|---|---|
| WO | WO 01/94632 A2 | 12/2001 |
| WO | WO 2004/020654 A2 | 3/2004 |
| WO | WO 2006/124771 A2 | 11/2006 |

OTHER PUBLICATIONS

Balnaves et al. (1991) "Direct PCR from CVS and blood lysates for detection of cystic fibrosis and Duchenne muscular dystrophy deletions," *Nucl. Acids. Res.*, 19(5):1155.

Baner et al. (1998) "Signal amplification of padlock probes by rolling circle replication," *Nucleic Acids Res.* 26(22):5073-5078.

Bortolin et al. (2004) "Analytical validation of the tag-it high-throughput microsphere-based universal array genotyping platform: application to the multiplex detection of a panel of thrombophilia-associated single-nucleotide polymorphisms," *Clin. Chem.*, 50(11):2028-2036.

Branton et al. (2008) "The potential and challenges or nanopore sequencing" *Nature Biotech* 26(10):1146-1153.

Burris et al. (1999) "A novel method for analysis of nuclear receptor function at natural promoters: peroxisome proliferator-activated receptor y agonist actions on aP2 gene expression detected using branched DNA messenger RNA quantitation," *Molecular Endocrinology*, 13(3):410-417.

Bushnell et al. (1999) "ProbeDesigner: for the design of probe sets for branched DNA (bDNA) signal amplification assays," *Bioinformatics*, 15(5):348-355.

Chothia (1992) "Proteins. One thousand families for the molecular biologist," *Nature*, 357(6379):543-544.

Collins et al. (1997) "A branched DNA signal amplification assay for quantification of nucleic acid targets below 100 molecules/ml," *Nucleic Acids Research*, 25(15):2979-2984.

Collins et al. (1998) "Branched DNA (bDNA) technology for direct quantification of nucleic acids: design and performance," in *Gene Quantification*, F. Ferre, ed.

Das & Smith (2000) "Identifying nature's protein Lego set," Adv. Protein Chem., 54:159-183.

De Vries et al. (2001) "PCR on cell lysates obtained from whole blood circumvents DNA isolation," *Clin. Chem.* 47(9):1701-1702.

Dhiman et al. (2009) "Next-generation sequencing: A transformative tool for vaccinology" Expert Rev. Vaccines, 8(8):963-967.

Dimitrov and Zuker (2004) "Prediction of hybridization and melting for double-stranded nucleic acids," *Biophysical Journal*, 87(1):215-226.

Edwards et al. (1991) Oligodeoxyribonucleotide ligation to single-stranded cDNAs: a new tool for cloning 5' ends of mRNAs and for constructing cDNA libraries by in vitro amplification, Nucleic Acids Res., 19(19):5227-5232.

Eid et al. (2009) "Real-time DNA sequencing from single polymerase molecules," Science 323(5910):133-138.

Elsner and Lindblad (1989) "Ultrasonic degradation of DNA," DNA 8(10):697-701.

Flagella et al. (2006) "A multiplex branched DNA assay for parallel quantitative gene expression profiling," *Anal. Biochem.*, 352(1):50-60.

Fulton et al. (1997) "Advanced multiplexed analysis with the FlowMetrix system," *Clin Chem.*, 43:1749-1756.

Genospectra "Product Information Sheet for QuantiGene Plex Human Apoptosis Panel 1,"product literature, Oct. 14, 2004, pp. 1-2.

Genospectra "Product Information Sheet for QuantiGene Plex Human Apoptosis Panel 2,"product literature, Oct. 14, 2004, pp. 1-2.

Genospectra "Product Information Sheet for QuantiGene Plex Human Cytokine Panel 1,"product literature, Oct. 14, 2004, pp. 1-2.

Genospectra "QuantiGene Plex brochure," product literature, Oct. 14, 2004, pp. 1-4.

Genospectra "QuantiGene Plex panel brochure," product literature, Oct. 14, 2004, p. 1.

Genospectra "QuantiGene® Plex Reagent System Instruction Manual," product literature, Oct. 14, 2004, pp. 1-26.

Gentalen & Chee. (1999) "A novel method for determining linkage between DNA sequences: hybridization to paired probe arrays," *Nucleic Acids Research*, 27(6):1485-1491.

Gnirke et al. (2009) "Solution hybrid selection with ultra-long oligonucleotides for massively parallel targeted sequencing," Nature Biotechnology, 27(2):182-189.

Hartley and Klaassen (2000) "Detection of chemical-induced differential expression of rat hepatic cytochrome P450 mRNA transcripts using branched DNA signal amplification technology," *Drug Metabolism and Disposition*, 28(5):608-616.

Hatch et al. (1999) "Rolling circle amplification of DNA immobilized on solid surfaces and its application to multiplex mutation detection," *Genetic Anal.-Biomedical Engineering*, 15(2):35-40.

Higuchi (1989) "DNA from whole blood for PCR," *Amplifications*, 2:1-3 (One page from The Jackson Library, http://www.jax.org.imr.whole_blood.html).

Hodeges et al. (2007) "Genome-wide in situ exon capture for selective resequencing," Nature Genetics, 39(12):1522-1527.

Hoppman-Chaney et al. (2010) "Evaluation of Oligonucleotide Sequence Capture Arrays and Comparison of Next-Generation Sequencing Platforms for Use in Molecular Diagnostics," Clinical Chemistry, 56(8): 1297-1306.

Iannone (2000) "Multiplexed single nucleotide polymorphism genotyping by oligonucleotide ligation and flow cytometry," *Cytometry*, 39(2):131-140.

Kern et al. (1996) "An enhanced-sensitivity branched-DNA assay for quantification of human immunodeficiency virus type 1 RNA in plasma," *J. Clin. Microbiol.*, 34(12):3196-3202.

Lewin & Stewart-Haynes (1992) "A simple method for DNA extraction from leukocytes for use in PCR," *BioTechniques*, 13(4):522-524.

(56) References Cited

OTHER PUBLICATIONS

Li et al. (2000) "The FHA domain mediates phosphoprotein interactions," *J. Cell. Sci.*, 113, Pt 23:4143-4149.
Lo et al. (2000) "Fetal DNA in maternal plasma: biology and diagnostic applications," *Clinical Chemistry*, 46(12):1903-1906.
Malygin et al. (1996) "Hybridization of two oligodeoxynucleotides to both strands of an RNA hairpin structure increases the efficiency of RNA-DNA duplex formation," *FEBS Letters*, 392:114-116.
Mercier et al. (1990) "Direct PCR from whole blood, without DNA extraction," *Nucl. Acids. Res.*, 18(19):5908.
Metzker (2010) "Sequencing technologies—The next generation," Nature Reviews Genetics, 11:31-46.
Nallur et al. (2001) "Signal amplification by rolling circle amplification on DNA microarrays," *Nucleic Acids Res.*, 29(23):E118.
Narayanan (1992) "Overview of principles and current uses of DNA probes in clinical and laboratory medicine," *Ann. Clin. Lab. Sci.*, 22(6):353-376.
Nolte (1998) "Branched DNA signal amplification for direct quantitation of nucleic acid sequences in clinical specimens," *Advances in Clinical Chemistry*, 33(1):201-235.
Nordvag et al. (1992) "Direct PCR of washed blood cells," *BioTechniques*, 12(4):490-493.
Okou et al. (2007) "Microarray-based genomic selection for high-throughput resequencing," Nature Methods, 4(11):907-909.
Player et al. (2001) "Single-copy gene detection using branched DNA (bDNA) in-situ hybridization," *The Journal of Histochemistry and Cytochemistry*, 49(5):603-611.
Porreca et al. (2007) "Multiplex amplification of large sets of human exons," Nature Methods, 4(11):931-936.
Schweitzer & Kingsmore (2001) "Combining nucleic acid amplification and detection," *Curr. Op Biotechnol.*, 12(1):21-27.
Shah et al. (1994) "Novel, ultrasensitive, Q-beta, replicase-amplified hybridization assay for detection of *Chlamydia trachomatis*," *J. Clin. Microbiol.*, 32(11):2718-2724.
Shah et al. (1995) "Detection of *Mycobacterium tuberculosis* directly from spiked human sputum by Q-beta replicase-amplifiied assay," *J. Clin. Microbiol.*, 33(2):322-328.
Shah et al. (2003) "Ultra-sensitive and specific detections of porcine endogenous retrovirus (PERV) using a sequence-capture real-time PCR approach," *J. Virol.Meth.*, 109:209-216.
Shen et al. (1998) "Quantification of cytokine mRNA in peripheral blood mononuclear cells using branched DNA (bDNA) technology," *J. Immunol. Meth.*, 215(1-2):123-134.
Stone et al. (1996) "Detection of rRNA from four respiratory pathogens using an automated Qβ replicase assay," *Mol. Cell. Probes*, 10:359-370.
Tessier et al. (1986) "Ligation of single-stranded oligodeoxyribonucleotides by T4 RNA ligase," Anal. Biochem., 158(1):171-178.
Travers et al. (2010) "A flexible and efficient template format for circular consensus sequencing and SNP detection," Nucl. Acids Res., 38(15):e159.
Tsai et al. (2003) "Nucleic acid capture assay, a new method for direct quantitation of nucleic acids," *Nucleic Acids Research*, 31(6):e25.
Turner et al. (2009) "Next-generation sequencing of vertebrate experimental organisms," Mamm. Genome, 20:327-338.
Ugozzoli et al. (1992) "Detection of specific alleles by using allele-specific primer extension followed by capture on solid support," *GATA*, 9(4):107-112.
Van Cleve et al. (1998) "Direct quantification of HIV by flow cytometry using branched DNA signal amplification," *Molecular and Cellular Probes*, 12:243-247.
Voelkerding et al. (2009) "Next-generation sequencing: From basic research to diagnostics," Clin. Chem., 55(4):641-658.
Wang et al. (1997) "Regulation of insulin preRNA splicing by glucose," Proc. Nat. Acad. Sci. USA, 94(9):4360-4365.
Wilber & Urdea (1998) "Quantification of HCV RNA in clinical specimens by branched DNA (bDNA) technology," *Methods in Molecular Medicine: Hepatitis C* 19:71-78.
Wilson et al. (2005) "A multiplexed PCR-coupled liquid bead array for the simultaneous detection of four biothreat agents," *Mol. Cell. Probes*, 19(2):137-144.
Yaffe & Elia (2001) "Phosphoserine/threonine-binding domains," Curr. Opin. Cell. Biol., 13(2):131-138.
Yang et al. (2001) "BADGE, Beads Array for the Detection of Gene Expression, a high-throughput diagnostic bioassay," *Genome Res.*, 11(11):1888-1898.
Zhang and Chiang (1996) "Single-stranded DNA ligation by T4 RNA ligase for PCR cloning of 5'-noncoding fragments and coding sequence of a specific gene," Nuc. Acids Res., 24(5):990-991.
Zhang et al. (2005) "Small interfering RNA and gene expression analysis using a multiplex branched DNA assay without RNA purification," *Journal for Biomolecular Screening*, 10(6):549-556.
Zolg et al. (1988) "High salt lysates: a simple method to store blood samples without refrigeration for subsequent use with DNA probes," Am. J. Trop. Med. Hyg., 39(1):33-40.

* cited by examiner

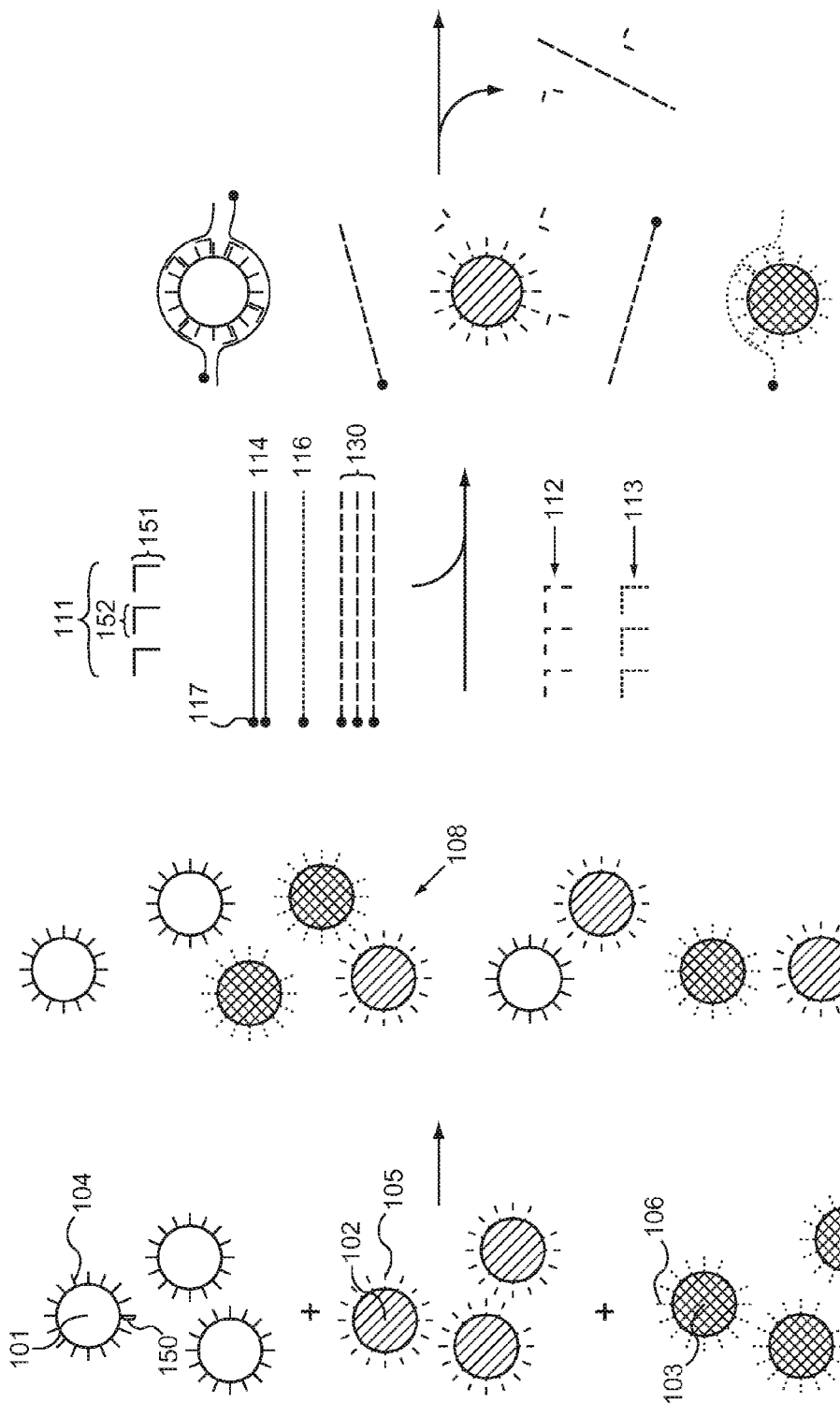

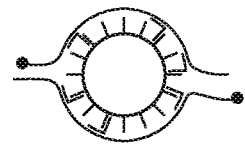 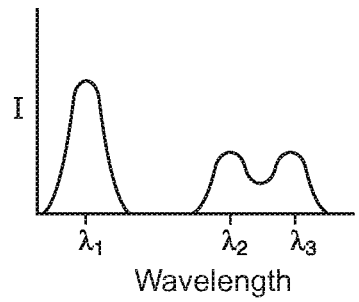
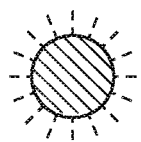 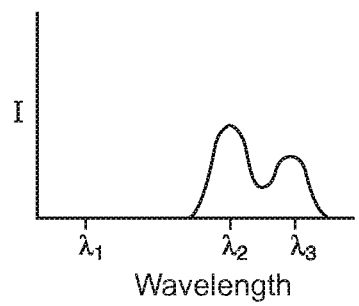
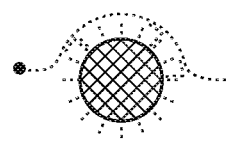 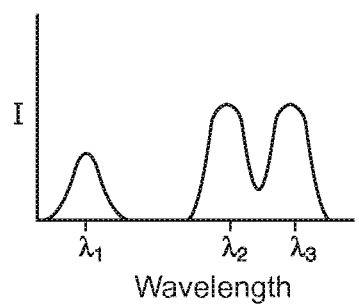
Fig. 1D

MULTIPLEX CAPTURE OF NUCLEIC ACIDS

CROSS-REFERENCE TO RELATED APPLICATIONS

This application is a continuation of U.S. patent application Ser. No. 12/930,041, filed Dec 23, 2010, which is a continuation-in-part of U.S. patent application Ser. No. 11/431,092, filed May 8, 2006, entitled "MULTIPLEX CAPTURE OF NUCLEIC ACIDS" by Luo et al, which claims priority to and benefit of the following prior provisional patent application: U.S. Ser. No. 60/679,500, filed May 9, 2005, entitled "MULTIPLEX CAPTURE OF NUCLEIC ACIDS" by Luo and Yang. Each of these applications is incorporated herein by reference in its entirety for all purposes.

FIELD OF THE INVENTION

The present invention is in the field of nucleic acid hybridization. The invention includes methods for capturing nucleic acids, including capture of two or more nucleic acids simultaneously from a single sample, capture of long nucleic acids, and capture of one or more nucleic acids for subsequent isolation and/or manipulation such as sequencing. The invention also includes compositions and kits related to the methods.

BACKGROUND OF THE INVENTION

A variety of techniques for detection of nucleic acids involve capture of the nucleic acids to a surface through hybridization of each nucleic acid to an oligonucleotide (or other nucleic acid) that is attached to the surface. For example, DNA microarray technology, which is widely used to analyze gene expression, relies on hybridization of DNA targets to preformed arrays of polynucleotides. See, e.g., Lockhart and Winzeler (2000) "Genomics, gene expression and DNA arrays" Nature 405:827-36, Gerhold et al. (2001) "Monitoring expression of genes involved in drug metabolism and toxicology using DNA microarrays" Physiol Genomics 5:161-70, Thomas et al. (2001) "Identification of toxicologically predictive gene sets using cDNA microarrays" Mol Pharmacol 60:1189-94, and Epstein and Butow (2000) "Microarray technology—enhanced versatility, persistent challenge" Curr Opin Biotechnol. 11:36-41.

A typical DNA microarray contains a large number of spots, with each spot containing a single oligonucleotide intended to hybridize to a particular nucleic acid target. For example, the GeneChip® microarray available from Affymetrix (Santa Clara, Calif.) includes thousands of spots, with each spot containing a different single 25 mer oligonucleotide. Multiple (e.g., about 20) oligonucleotides that are perfect matches for a particular target nucleic acid are typically provided, with each oligonucleotide being complementary to a different region of the target nucleic acid. Additional spots including mismatch oligonucleotides having a single nucleotide substitution in the middle of the oligonucleotide are also included in the array. Since binding to a single 25 mer may not result in specific capture of the target nucleic acid, statistical methods are used to compare the signals obtained from all the spots for a particular target nucleic acid (e.g., perfectly matched and mismatched oligonucleotides) to attempt to correct for cross-hybridization of other nucleic acids to those spots.

In another approach, longer probes are used to form the spots in the microarray. For example, instead of short oligonucleotides, longer oligonucleotides or cDNAs can be used to capture the target nucleic acids. Use of such longer probes can provide increased specificity, but it can also make discrimination of closely related sequences difficult.

DNA microarray technology has also been employed for enrichment of specific sequences for high throughput sequencing. Next-generation sequencing platforms facilitate large scale sequencing efforts, e.g., for detection of polymorphisms, association studies, mapping, or detection of somatic mutations. However, such efforts still require simplification of the target population, e.g., to include only a subset of the genome. While microarray hybridization can be used to prepare samples for sequencing, concerns regarding specificity are similar to those discussed for gene expression analysis. In addition, microarray-based capture can be time-consuming, require relatively large amounts of starting material, and involve additional processing steps such as enzymatic amplification of the captured DNA.

Improved methods for capturing target nucleic acids to surfaces are thus desirable. Among other aspects, the present invention provides methods that overcome the above noted limitations and permit rapid, simple, and highly specific capture of nucleic acids, including simultaneous capture of multiple nucleic acids, capture of long nucleic acids, and capture of nucleic acids for sequence analysis. A complete understanding of the invention will be obtained upon review of the following.

SUMMARY OF THE INVENTION

In one aspect, the present invention provides methods of capturing nucleic acids. Nucleic acids are captured on a solid support through cooperative hybridization events. Where multiple nucleic acids are captured simultaneously, they can be captured together or different nucleic acids can be captured on different distinguishable subsets of particles or at different selected positions on a spatially addressable solid support. Capture is optionally followed by isolation and/or manipulation of the captured nucleic acids, e.g., determination of their polynucleotide sequence. Compositions and kits related to the methods are also provided.

A first general class of embodiments provides methods of capturing two or more nucleic acids of interest, generally different nucleic acids. In the methods, a sample, a solid support, and two or more subsets of n target capture probes (typically n different target capture probes), wherein n is at least two, are provided. The sample comprises or is suspected of comprising the nucleic acids of interest. A support capture probe is associated with the solid support. A different subset of target capture probes is provided for each different nucleic acid of interest. The target capture probes in each subset are capable of hybridizing to nonoverlapping polynucleotide sequences in the corresponding nucleic acid of interest. The target capture probes in each subset are also capable of hybridizing to the support capture probe.

Any nucleic acid of interest present in the sample is hybridized to its corresponding subset of n target capture probes, and the subset of n target capture probes is hybridized to the support capture probe, thereby capturing the nucleic acid on the solid support. The hybridizing the subset of n target capture probes to the support capture probe is performed at a hybridization temperature which is greater than a melting temperature $T_m$ of a complex between each individual target capture probe and the support capture probe.

In some embodiments, for example, where the different nucleic acids are to be separately isolated or detected, different nucleic acids are captured via different support capture probes to different distinguishable subsets of particles or to different preselected positions on a spatially addressable solid support. In other embodiments, for example, where the different nucleic acids are to be processed simultaneously after their capture, the different nucleic acids are captured to a single solid support through binding of their target capture probes to a single type of support capture probe.

Thus, in one class of embodiments, the solid support comprises particles of a single type, which particles bear the support capture probe. In another class of embodiments, the solid support comprises a surface of a well of a multiwell plate bearing the support capture probe.

The nucleic acids can be removed from the solid support after their capture, e.g., after washing the support to remove any unbound nucleic acids. Target capture probes are optionally separated from the captured nucleic acids. In one class of embodiments, the target capture probes are separated from the captured nucleic acids based on their relative sizes, e.g., by gel or capillary electrophoresis, affinity binding (e.g., to a silica membrane or particles), ultrafiltration, or similar techniques. In a related class of embodiments, the target capture probes are selectively degraded.

The captured nucleic acids can be manipulated, optionally after their removal from the solid support and/or separation from the target capture probes. Manipulation can include enzymatic manipulation, e.g., restriction enzyme digestion, ligation, or amplification of one or more of the captured nucleic acids or a portion thereof by PCR, insertion into a vector, transformation or transfection into a host cell, and/or similar techniques well known in the art for manipulation of nucleic acids. In one exemplary class of embodiments, a polynucleotide sequence of one or more of the captured nucleic acids or a portion thereof is determined. Essentially any technique can be employed for determining the polynucleotide sequence, including, but not limited to, sequencing by synthesis, sequencing by cyclic reversible termination, sequencing by single nucleotide addition, real-time sequencing, dideoxy sequencing, sequencing by ligation, sequencing by hybridization, single molecule sequencing, or nanopore sequencing. As discussed in greater detail hereinbelow, the methods are useful for performing a chromosome walk, capturing desired targets for resequencing, or for capturing nucleic acids of particular interest for sequencing (e.g., members of the gene or protein family, nucleic acids including a conserved motif, genes implicated in a disease process or in response to treatment, etc.).

Essentially any type (or combination of types) of nucleic acids can be captured using the methods of the invention. For example, in one class of embodiments the two or more different nucleic acids of interest are two or more different DNAs, e.g., two or more different fragments of genomic or mitochondrial DNA. In another class of embodiments, the two or more different nucleic acids of interest are two or more different RNAs. Optionally, the two or more different nucleic acids of interest represent two or more different exons. Similarly, the two or more different nucleic acids of interest can represent two or more different introns.

Similarly, the nucleic acids can be of varying lengths, including lengths greater than those generally captured by current techniques. Thus, in one class of embodiments, at least one of the nucleic acids of interest is at least 20 kilobases in length, e.g., at least 50 kilobases, at least 100 kilobases, at least 250 kilobases, or at least 500 kilobases in length.

A captured nucleic acid can be detected and optionally quantitated, e.g., by incorporation of a label into the nucleic acid, binding of a detection probe, amplification, or the like, as described hereinbelow.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, or even 100 or more nucleic acids of interest. A like number of subsets of target capture probes is typically provided; thus, the two or more subsets of n target capture probes can comprise five or more, 10 or more, 20 or more, 30 or more, 40 or more, 50 or more, or even 100 or more subsets of n target capture probes.

As noted, each of the two or more subsets of target capture probes includes n target capture probes, where n is at least two. Preferably, n is at least three, and n can be at least four or at least five or more. Typically, but not necessarily, n is at most ten.

Each target capture probe is capable of hybridizing to the support capture probe. The target capture probe typically includes a polynucleotide sequence U-1 that is complementary to a polynucleotide sequence U-2 in the support capture probe. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive).

As noted, the hybridizing the subset of n target capture probes to the support capture probe is performed at a hybridization temperature which is greater than a melting temperature $T_m$ of a complex between each individual target capture probe and the support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$. Hybridization of the target capture probes to the nucleic acids of interest and to the support capture probe can occur simultaneously or in either order.

At any of various steps, materials not captured on the solid support are optionally separated from the support. For example, after the target capture probes, nucleic acids, and support-bound support capture probe are hybridized, the solid support is optionally washed to remove unbound nucleic acids and target capture probes.

The methods can be used to capture the nucleic acids of interest from essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen.

Another general class of embodiments provides a composition that includes a solid support having associated therewith a support capture probe. The composition also includes two or more subsets of n target capture probes (typically, n different target capture probes), wherein n is at least two. A different subset of target capture probes is provided for each different nucleic acid of interest, and the target capture probes in each subset are capable of hybridizing to nonoverlapping polynucleotide sequences in the corresponding nucleic acid of interest. The target capture probes in each subset are also capable of hybridizing to the support capture probe.

The composition optionally includes the two or more different nucleic acids of interest. Optionally, the composition is maintained at a hybridization temperature, which hybridization temperature is greater than a melting temperature $T_m$ of a complex between each individual target capture probe and the support capture probe, and the nucleic acids of interest are hybridized to the target capture probes, which target capture probes are hybridized to the support capture probe.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, type of solid support (e.g., different subsets of distinguishable particles bearing different support capture probes, a single type of particle bearing a single support capture probe, a multiwell plate, or a spatially addressable solid support), label configuration, source of the sample and/or nucleic acids, and/or the like. The composition is optionally used to purify the nucleic acids of interest for further manipulation, e.g., prior to sequencing.

A related aspect provides methods that facilitate capture of nucleic acids longer than those readily accessible to current capture techniques. Accordingly, one general class of embodiments includes methods of capturing long nucleic acids. In the methods, a sample, a solid support, and one or more subset of n target capture probes (typically n different target capture probes), wherein n is at least two, are provided. The sample comprises or is suspected of comprising one or more nucleic acid of interest, which nucleic acid is at least 20 kilobases in length. The solid support comprises a support capture probe associated with the support. The target capture probes in each subset are capable of hybridizing to nonoverlapping polynucleotide sequences in the corresponding nucleic acid of interest, and the target capture probes in each subset are also capable of hybridizing to the support capture probe. Any nucleic acid of interest present in the sample is hybridized to its corresponding subset of n target capture probes, and the subset of n target capture probes is hybridized to the support capture probe, thereby capturing the nucleic acid on the solid support. Hybridizing the subset of n target capture probes to the support capture probe is performed at a hybridization temperature which is greater than a melting temperature $T_m$ of a complex between each individual target capture probe and the support capture probe.

The one or more nucleic acid of interest can be, e.g., 20-30 kilobases in length, 30-40 kilobases in length, 40-50 kilobases in length, at least 50 kilobases in length, at least 75 kilobases in length, at least 100 kilobases in length, at least 250 kilobases in length, or even at least 500 kilobases in length. Despite the length of the nucleic acid to be captured, the target capture probes are optionally clustered within a small region of the nucleic acid. For example, the subset of n target capture probes optionally hybridizes within a region of the corresponding nucleic acid of interest that is less than 1000 bases, e.g., less than 750 bases, less than 600 bases, or less than 500 bases in length. In other embodiments, the target capture probes can be distributed along the entire length of the nucleic acid of interest, clustered at the two ends, or the like.

As for the embodiments described above, the solid support can be essentially any suitable support, including, but not limited to, particles (e.g., a single type of particles bearing a single support capture probe or two or more subsets of distinguishable particles bearing different support capture probes), a spatially addressable solid support bearing different support capture probes at different predetermined positions on the support, or a surface of a well of a multiwell plate.

Essentially any type of long nucleic acid can be captured using the methods, including, e.g., DNA, e.g., one or more fragments of genomic or mitochondrial DNA. The DNA fragments can be overlapping, contiguous, non-contiguous, or even derived from two or more different sources. Thus, in one exemplary class of embodiments, the one or more nucleic acid of interest comprises at least two overlapping fragments of genomic DNA, which overlapping fragments each include a region complementary to the n target capture probes. Optionally, the nucleic acids of interest include two or more sets of genomic DNA fragments (typically overlapping within but not necessarily between the sets), where each set includes a different region complementary to a different set of n target capture probes.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, label configuration, source of the sample and/or nucleic acids, hybridization temperature, subsequent isolation or manipulation of the nucleic acids, and/or the like. For example, the methods can include determining a polynucleotide sequence of the captured nucleic acid or a portion thereof.

Yet another general class of embodiments provides a composition that includes one or more nucleic acid of interest, which nucleic acid is at least 20 kilobases in length, a solid support having associated therewith a support capture probe, and one or more subset of n target capture probes (e.g., n different target capture probes), wherein n is at least two. The target capture probes in each subset are capable of hybridizing to nonoverlapping polynucleotide sequences in the corresponding nucleic acid of interest, and are also capable of hybridizing to the support capture probe.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, type of solid support, label configuration, type and length of nucleic acids of interest, source of the sample and/or nucleic acids, and/or the like.

One general class of embodiments provides methods of isolating one or more nucleic acid. In the methods, a sample, a pooled population of particles, and five or more subsets of at least two different target capture probes are provided. The sample comprises five or more different nucleic acids of interest. The pooled population of particles includes five or more subsets of particles. The particles in each subset have associated therewith a different support capture probe. A different subset of target capture probes is provided for each different nucleic acid of interest. The at least two different target capture probes in each subset are capable of hybridizing to nonoverlapping polynucleotide sequences in the corresponding nucleic acid of interest, and the target capture probes in each subset are also capable of hybridizing to a different one of the support capture probes and thereby associating each subset of target capture probes with a different selected subset of the particles. Each nucleic acid of interest can thus, by hybridizing to its corresponding subset of target capture probes which are in turn hybridized to a corresponding support capture probe, be associated with an identifiable subset of the particles.

For each of the nucleic acids of interest, the nucleic acid is hybridized to its corresponding subset of at least two target capture probes and the subset of target capture probes is hybridized to its corresponding support capture probe, thereby capturing the nucleic acid on the subset of particles with which the target capture probes are associated. The hybridizing the subset of target capture probes to the corresponding support capture probe is performed in the presence of the nucleic acid and at a hybridization temperature which is greater than a melting temperature $T_m$ of a complex between each individual target capture probe and its corresponding support capture probe.

One or more subsets of particles is isolated, whereby any nucleic acid of interest captured on the particles is isolated, e.g., using a flow cytometer, particle sorter, or similar instrument. The isolated nucleic acid can optionally be removed from the particles, e.g., by eluting the nucleic acid from the particles (e.g., by heat or chemical denaturation or by selectively degrading the capture probes), optionally after washing the isolated one or more subsets of particles to remove any unbound or non-specifically bound materials. The isolated nucleic acid is subjected to further manipulation, e.g., enzymatic manipulation, including, but not limited to, PCR amplification of the isolated nucleic acid or a portion thereof, restriction enzyme digestion of the isolated nucleic acid, or ligation of the isolated nucleic acid. As other examples, manipulation of the isolated nucleic acid can include introduction into a cloning or expression vector, transformation or transfection into a host cell, or determination of a polynucleotide sequence of the isolated nucleic acid or a portion thereof.

Essentially all of the features noted for the other embodiments herein apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

Another general class of embodiments also includes methods of isolating one or more nucleic acids. In the methods, a sample, a solid support, and five or more subsets of at least two different target capture probes are provided. The sample comprises five or more different nucleic acids of interest. The solid support comprises five or more different support capture probes, each of which is provided at a different selected position on the solid support. A different subset of target capture probes is provided for each different nucleic acid of interest. The at least two different target capture probes in each subset are capable of hybridizing to nonoverlapping polynucleotide sequences in the corresponding nucleic acid of interest, and the target capture probes in each subset are also capable of hybridizing to a different one of the support capture probes and thereby associating each subset of target capture probes with a different selected position on the solid support. Each nucleic acid of interest can thus, by hybridizing to its corresponding subset of target capture probes which are in turn hybridized to a corresponding support capture probe, be associated with, e.g., a known, predetermined location on the solid support.

For each of the nucleic acids of interest, the nucleic acid is hybridized to its corresponding subset of at least two target capture probes and the subset of target capture probes is hybridized to its corresponding support capture probe, thereby capturing the nucleic acid on the solid support at the selected position with which the target capture probes are associated. Hybridizing the subset of target capture probes to the corresponding support capture probe is performed at a hybridization temperature which is greater than a melting temperature $T_m$ of a complex between each individual target capture probe and its corresponding support capture probe.

The nucleic acid captured at one or more of the selection positions is isolated (e.g., by removal of that portion of the support) and typically removed from the support (e.g., by eluting the nucleic acid by heat or chemical denaturation or by selectively degrading the capture probes, optionally after washing the support to remove any unbound or non-specifically bound materials). The isolated nucleic acid is subjected to further manipulation, e.g., enzymatic manipulation, including, but not limited to, PCR amplification of the isolated nucleic acid or a portion thereof, restriction enzyme digestion of the isolated nucleic acid, or ligation of the isolated nucleic acid. As other examples, manipulation of the isolated nucleic acid can include introduction into a cloning or expression vector, transformation or transfection into a host cell, or determination of a polynucleotide sequence of the isolated nucleic acid or a portion thereof.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, type of support, label configuration, source of the sample and/or nucleic acids, and/or the like.

Capture of nucleic acids through cooperative hybridization is a useful means of purifying them for subsequent manipulation, such as sequencing. Accordingly, one general class of embodiments provides methods of sequencing one or more nucleic acids of interest. In the methods, a sample that comprises or is suspected of comprising the one or more nucleic acids of interest is provided, as is a solid support that has associated therewith a support capture probe. One or more subsets of n target capture probes (typically n different target capture probes), wherein n is at least two, are also provided (e.g., a different subset for each different nucleic acid of interest or for each different set of overlapping nucleic acids, where each set includes a region complementary to one subset of the target capture probes). The target capture probes in each subset are capable of hybridizing to nonoverlapping polynucleotide sequences in the corresponding nucleic acid of interest. The target capture probes in each subset are also capable of hybridizing to the support capture probe.

For each of the nucleic acids of interest, the nucleic acid is hybridized to its corresponding subset of n target capture probes, and the subset of n target capture probes is hybridized to the support capture probe, thereby capturing the nucleic acid on the solid support. The hybridizing the subset of n target capture probes to the support capture probe is performed at a hybridization temperature which is greater than a melting temperature $T_m$ of a complex between each individual target capture probe and the support capture probe. A polynucleotide sequence of the captured nucleic acids or a portion thereof is determined.

Suitable solid supports are well known in the art. Optionally, different nucleic acids (or different sets of nucleic acids that include a common region complementary to a subset of target capture probes) are captured to different distinguishable subsets of particles or to different preselected positions on a spatially addressable solid support as described herein. Typically, however, the nucleic acids of interest are processed simultaneously after their capture and can thus be captured collectively. Accordingly, different nucleic acids are optionally captured to a single solid support through binding of their target capture probes to a single type of support capture probe. For example, in one class of embodiments, the solid support comprises particles of a single type, which particles bear the support capture probe. In another class of embodiments, the solid support comprises a surface of a well of a multiwell plate bearing the support capture probe.

The nucleic acids can be removed from the solid support after their capture, e.g., after washing the support to remove any unbound nucleic acids. Target capture probes are optionally separated from the captured nucleic acids. In one class of embodiments, the target capture probes are separated from the captured nucleic acids based on their relative sizes, e.g., by gel or capillary electrophoresis, affinity binding (e.g., to a silica membrane or particles), ultrafiltration, or similar techniques. In a related class of embodiments, the target capture probes are selectively degraded.

The captured nucleic acids can but need not be manipulated, optionally after their removal from the solid support and/or separation from the target capture probes, prior to sequencing. Such manipulation can include enzymatic manipulation, e.g., restriction enzyme digestion, ligation (e.g., to oligonucleotide adapters), or amplification of one or more of the captured nucleic acids or a portion thereof by PCR, insertion into a vector, transformation or transfection into a host cell, and/or similar techniques well known in the art for manipulation of nucleic acids.

Essentially any technique can be employed for determining the polynucleotide sequence, including, but not limited to, sequencing by synthesis, sequencing by cyclic reversible termination, sequencing by single nucleotide addition, real-time sequencing, dideoxy sequencing, sequencing by ligation, sequencing by hybridization, single molecule sequencing, or nanopore sequencing. As discussed in greater detail hereinbelow, the methods are useful for performing a chromosome walk, capturing desired targets for resequencing, or for capturing nucleic acids of particular interest for sequencing (e.g., members of a gene or protein family, nucleic acids including a conserved motif, genes implicated in a disease process or in response to treatment, etc.).

Essentially any type (or combination of types) of nucleic acids can be isolated and sequenced using the methods of the invention. For example, in one class of embodiments the one or more nucleic acids of interest are one or more DNAs, e.g., one or more fragments of genomic or mitochondrial DNA. Where two or more fragments of DNA are captured and sequenced, the DNA fragments can be overlapping, contiguous, non-contiguous, or even derived from two or more different sources. Thus, in one exemplary class of embodiments, the one or more nucleic acid of interest comprises at least two overlapping fragments of genomic DNA, which overlapping fragments each include a region complementary to the n target capture probes. Optionally, the nucleic acids of interest include two or more sets of genomic DNA fragments (typically overlapping within but not necessarily between the sets), where each set includes a different region complementary to a different set of n target capture probes. In another class of embodiments, the two or more different nucleic acids of interest are two or more different RNAs. Optionally, the one or more nucleic acids of interest comprise two or more different nucleic acids of interest, which two or more different nucleic acids of interest represent two or more different exons. Similarly, the two or more different nucleic acids of interest can represent two or more different introns.

As noted, multiple nucleic acids can be captured simultaneously for sequencing. Thus, the one or more nucleic acids of interest optionally comprise two or more, five or more, 10 or more, 20 or more, 30 or more, 40 or more, 50 or more, or even 100 or more nucleic acids of interest. A like number of subsets of target capture probes is typically provided; thus, the one or more subsets of n target capture probes can comprise two or more, five or more, 10 or more, 20 or more, 30 or more, 40 or more, 50 or more, or even 100 or more subsets of n target capture probes.

Essentially all of the features noted for the embodiments above apply to these embodiments as well, as relevant; for example, with respect to number of target capture probes per subset, configuration of the target capture probes and/or support capture probes, source of the sample and/or nucleic acids, hybridization temperature, and/or the like.

BRIEF DESCRIPTION OF THE DRAWINGS

FIG. 1 Panels A-D schematically depict multiplex capture and detection of nucleic acids, where the nucleic acids of interest are captured on distinguishable subsets of microspheres and then detected.

Figure 2:
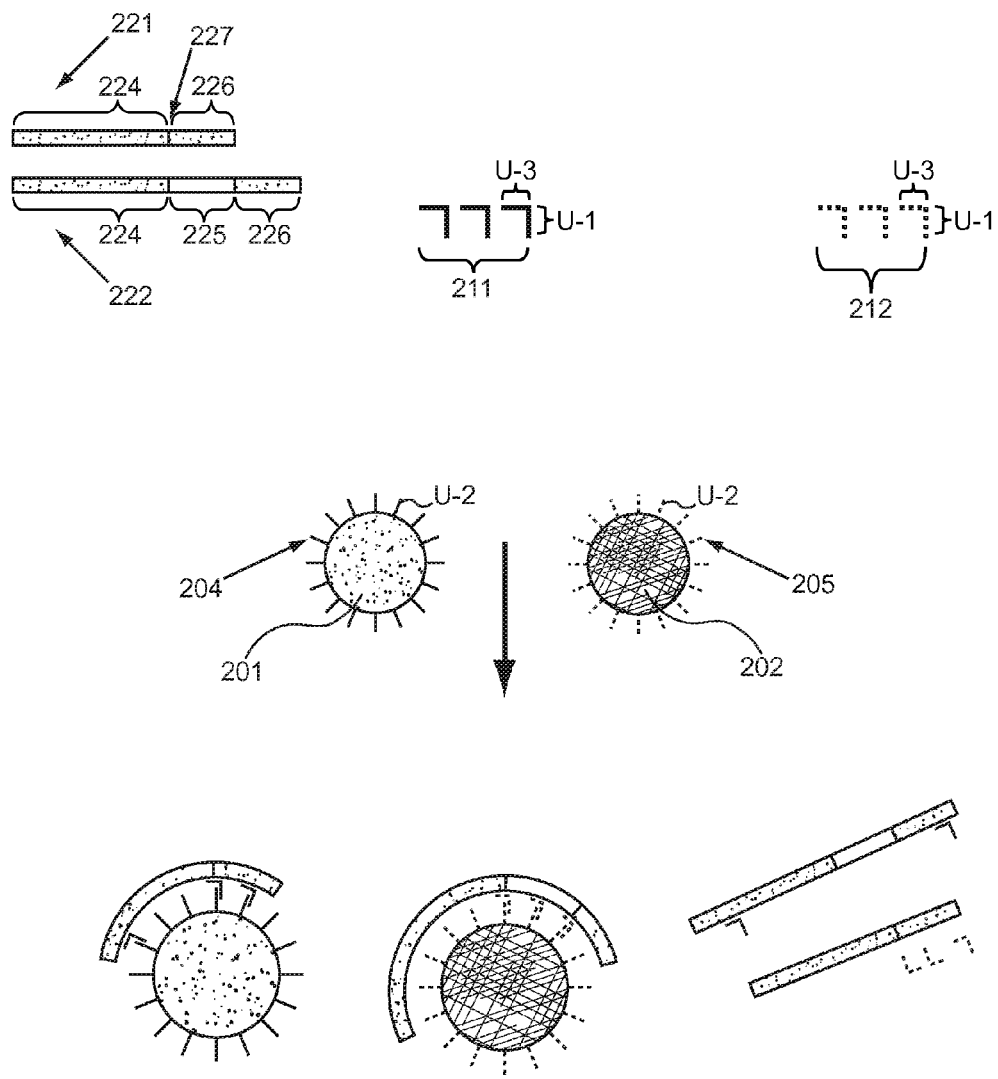
FIG. 2 schematically depicts an exemplary embodiment in which two splice variants are specifically captured on distinguishable subsets of microspheres.

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The "$T_m$" (melting temperature) of a nucleic acid duplex under specified conditions (e.g., relevant assay conditions) is the temperature at which half of the base pairs in a population of the duplex are disassociated and half are associated. The $T_m$ for a particular duplex can be calculated and/or measured, e.g., by obtaining a thermal denaturation curve for the duplex (where the $T_m$ is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "target capture probe" is a polynucleotide that is capable of hybridizing to a nucleic acid of interest and to a support capture probe. The target capture probe typically has a first polynucleotide sequence U-1, which is complementary to the support capture probe, and a second polynucleotide sequence U-3, which is complementary to a polynucleotide sequence of the nucleic acid of interest. Sequences U-1 and U-3 are typically not complementary to each other. The target capture probe is preferably single-stranded.

A "support capture probe" is a polynucleotide that is capable of hybridizing to at least one target capture probe and that is tightly bound (e.g., covalently or noncovalently, directly or through a linker, e.g., streptavidin-biotin or the like) to a solid support, a spatially addressable solid support, a slide, a particle, a microsphere, or the like. The support capture probe typically comprises at least one polynucleotide sequence U-2 that is complementary to polynucleotide sequence U-1 of at least one target capture probe. The support capture probe is preferably single-stranded.

A "label" is a moiety that facilitates detection of a molecule. Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "microsphere" is a small spherical, or roughly spherical, particle. A microsphere typically has a diameter less than about 1000 micrometers (e.g., less than about 100 micrometers, optionally less than about 10 micrometers).

A "microorganism" is an organism of microscopic or submicroscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

A variety of additional terms are defined or otherwise characterized herein.

DETAILED DESCRIPTION

The present invention provides methods, compositions, and kits for multiplex capture of nucleic acids. A particular nucleic acid of interest is captured to a surface through cooperative hybridization of multiple target capture probes to the nucleic acid. Each of the target capture probes has a first polynucleotide sequence that can hybridize to the target nucleic acid and a second polynucleotide sequence that can hybridize to a support capture probe that is bound to the surface. The temperature and the stability of the complex between a single target capture probe and its corresponding support capture probe can be controlled such that binding of a single target capture probe to a nucleic acid and to the support capture probe is not sufficient to stably capture the nucleic acid on the surface to which the support capture probe is bound, whereas simultaneous binding of two or more target capture probes to a nucleic acid can capture it on the surface. Requiring such cooperative hybridization of multiple target capture probes for capture of each nucleic acid of interest results in high specificity and low background from cross-hybridization of the target capture probes with other, non-target nucleic acids. Such low background and minimal cross-hybridization are typically substantially more difficult to achieve in multiplex than in single-plex capture of nucleic acids, because the number of potential nonspecific interactions are greatly increased in a multiplex experiment due to the increased number of probes used (e.g., the greater number of target capture probes). Requiring multiple simultaneous target capture probe-support capture probe interactions for the capture of a target nucleic acid minimizes the chance that nonspecific capture will occur, even when some nonspecific target-target capture probe and/or target capture probe-support capture probe interactions do occur.

The methods of the invention can be used for multiplex capture of two or more nucleic acids simultaneously, for example, from even complex samples, without requiring prior purification of the nucleic acids, when the nucleic acids are present at low concentration, and/or in the presence of other, highly similar nucleic acids. In one aspect, the methods involve capture of the nucleic acids to particles (e.g., distinguishable subsets of microspheres or microparticles), while in another aspect, the nucleic acids are captured to a spatially addressable solid support. After capture, the nucleic acids are optionally detected, amplified, isolated, sequenced, and/or the like. Compositions, kits, and systems related to the methods are also provided.

Methods

Multiplex Capture

A first general class of embodiments includes methods of capturing two or more nucleic acids of interest. In the methods, a sample, a pooled population of particles, and two or more subsets of n target capture probes, wherein n is at least two, are provided. The sample comprises or is suspected of comprising the nucleic acids of interest. The pooled population of particles includes two or more subsets of particles. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. Preferably, a plurality of the particles in each subset are distinguishable from a plurality of the particles in every other subset. (Typically, substantially all of the particles in each subset are distinguishable from substantially all of the particles in every other subset.) Each nucleic acid of interest can thus, by hybridizing to its corresponding subset of n target capture probes which are in turn hybridized to a corresponding support capture probe, be associated with an identifiable subset of the particles. Alternatively, the particles in the various subsets need not be distinguishable from each other (for example, in embodiments in which any nucleic acid of interest present is to be isolated, amplified, and/or detected, without regard to its identity, following its capture on the particles.)

The sample, the pooled population of particles, and the subsets of n target capture probes are contacted, any nucleic acid of interest present in the sample is hybridized to its corresponding subset of n target capture probes, and the subset of n target capture probes is hybridized to its corresponding support capture probe. The hybridizing the nucleic acid of interest to the n target capture probes and the n target capture probes to the corresponding support capture probe captures the nucleic acid on the subset of particles with which the target capture probes are associated. The hybridizing the subset of n target capture probes to the corresponding support capture probe is performed at a hybridization temperature which is greater than a melting temperature $T_m$ of a complex between each individual target capture probe and its corresponding support capture probe. Binding of a single target capture probe to its corresponding nucleic acid (or to an extraneous nucleic acid) and support capture probe is thus typically insufficient to capture the nucleic acid on the corresponding subset of particles. It will be evident that the hybridization temperature is typically less than a $T_m$ of a complex between the nucleic acid of interest, all n corresponding target capture probes, and the corresponding support capture probe.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, or even 100 or more nucleic acids of interest. A like number of subsets of particles and subsets of target capture probes are typically provided; thus, the two or more subsets of particles can comprise five or more, 10 or more, 20 or more, 30 or more, 40 or more, 50 or more, or even 100 or more subsets of particles, while the two or more subsets of n target capture probes can comprise five or more, 10 or more, 20 or more, 30 or more, 40 or more, 50 or more, or even 100 or more subsets of n target capture probes.

Essentially any suitable particles, e.g., particles to which support capture probes can be attached and which optionally have distinguishable characteristics, can be used. For example, in one preferred class of embodiments, the particles are microspheres. The microspheres of each subset can be distinguishable from those of the other subsets, e.g., on the basis of their fluorescent emission spectrum, their diameter, or a combination thereof. For example, the microspheres of each subset can be labeled with a unique fluorescent dye or mixture of such dyes, quantum dots with distinguishable emission spectra, and/or the like. As another example, the particles of each subset can be identified by an optical barcode, unique to that subset, present on the particles.

The particles optionally have additional desirable characteristics. For example, the particles can be magnetic, diamagnetic, superparamagnetic, or paramagnetic, which provides a convenient means for separating the particles from solution, e.g., to simplify separation of the particles from any materials not bound to the particles.

As noted, each of the two or more subsets of target capture probes includes n target capture probes, where n is at least two. Preferably, n is at least three, and n can be at least four or at least five or more. Typically, but not necessarily, n is at most ten. For example, n can be between three and ten, e.g., between five and ten or between five and seven, inclusive. Use of fewer target capture probes can be advantageous, for example, in embodiments in which nucleic acids of interest are to be specifically captured from samples including other nucleic acids with sequences very similar to that of the nucleic acids of interest. In other embodiments (e.g., embodiments in which capture of as much of the nucleic acid as possible is desired), however, n can be more than 10, e.g., between 20 and 50. n can be the same for all of the subsets of target capture probes, but it need not be; for example, one subset can include three target capture probes while another subset includes five target capture probes. The n target capture probes in a subset preferably hybridize to nonoverlapping polynucleotide sequences in the corresponding nucleic acid of interest. The nonoverlapping polynucleotide sequences can, but need not be, consecutive within the nucleic acid of interest. Blocking probes that hybridize to regions of the nucleic acid of interest not occupied by the target capture probes (or any detection probes that may be employed) are optionally employed.

Each target capture probe is capable of hybridizing to its corresponding support capture probe. The target capture probe typically includes a polynucleotide sequence U-1 that is complementary to a polynucleotide sequence U-2 in its corresponding support capture probe. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive). For example, U-1 and U-2 can be 14, 15, 16, or 17 nucleotides in length, or they can be between 9 and 13 nucleotides in length (e.g., for lower hybridization temperatures, e.g., hybridization at room temperature).

The support capture probe can include polynucleotide sequence in addition to U-2, or U-2 can comprise the entire polynucleotide sequence of the support capture probe. For example, each support capture probe optionally includes a linker sequence between the site of attachment of the support capture probe to the particles and sequence U-2 (e.g., a linker sequence containing 8 Ts, as just one possible example).

It will be evident that the amount of overlap between each individual target capture probe and its corresponding support capture probe (i.e., the length of U-1 and U-2) affects the $T_m$ of the complex between that target capture probe and support capture probe, as does, e.g., the GC base content of sequences U-1 and U-2. Typically, all the support capture probes are the same length (as are sequences U-1 and U-2) from subset of particles to subset. However, depending, e.g., on the precise nucleotide sequence of U-2, different support capture probes optionally have different lengths and/or different length sequences U-2, to achieve the desired $T_m$. Different support capture probe-target capture probe complexes optionally have the same or different $T_m$s.

It will also be evident that the number of target capture probes required for stable capture of a nucleic acid depends, in part, on the amount of overlap between the target capture probes and the support capture probe (i.e., the length of U-1 and U-2). For example, if n is 5-7 for a 14 nucleotide overlap, n could be 3-5 for a 15 nucleotide overlap or 2-3 for a 16 nucleotide overlap.

As noted, the hybridizing the subset of n target capture probes to the corresponding support capture probe is performed at a hybridization temperature which is greater than a melting temperature $T_m$ of a complex between each individual target capture probe and its corresponding support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Stable capture of nucleic acids of interest, e.g., while minimizing capture of extraneous nucleic acids (e.g., those to which n−1 or fewer of the target capture probes bind) can be achieved, for example, by balancing n (the number of target capture probes), the amount of overlap between the target capture probes and the support capture probe (the length of U-1 and U-2), and/or the stringency of the conditions under which the target capture probes, the nucleic acids, and the support capture probes are hybridized.

Appropriate combinations of n, amount of complementarity between the target capture probes and the support capture probe, and stringency of hybridization can, for example, be determined experimentally by one of skill in the art. For example, a particular value of n and a particular set of hybridization conditions can be selected, while the number of nucleotides of complementarity between the target capture probes and the support capture probe is varied until hybridization of the n target capture probes to a nucleic acid captures the nucleic acid while hybridization of a single target capture probe does not efficiently capture the nucleic acid. Similarly, n, amount of complementarity, and stringency of hybridization can be selected such that the desired nucleic acid of interest is captured while other nucleic acids present in the sample are not efficiently captured. Stringency can be controlled, for example, by controlling the formamide concentration, chaotropic salt concentration, salt concentration, pH, organic solvent content, and/or hybridization temperature.

As noted, the $T_m$ of any nucleic acid duplex can be directly measured, using techniques well known in the art. For example, a thermal denaturation curve can be obtained for the duplex, the midpoint of which corresponds to the $T_m$. It will be evident that such denaturation curves can be obtained under conditions having essentially any relevant pH, salt concentration, solvent content, and/or the like.

The $T_m$ for a particular duplex (e.g., an approximate $T_m$) can also be calculated. For example, the $T_m$ for an oligonucleotide-target duplex can be estimated using the following algorithm, which incorporates nearest neighbor thermodynamic parameters: Tm (Kelvin)=$\Delta H°/(\Delta S°+R \ln C_t)$, where the changes in standard enthalpy($\Delta H°$ and entropy ($\Delta S°$) are calculated from nearest neighbor thermodynamic parameters (see, e.g., SantaLucia (1998) "A unified view of polymer, dumbbell, and oligonucleotide DNA nearest-neighbor thermodynamics" Proc. Natl. Acad. Sci. USA 95:1460-1465, Sugimoto et al. (1996) "Improved thermodynamic parameters and helix initiation factor to predict stability of DNA duplexes" Nucleic Acids Research 24: 4501-4505, Sugimoto et al. (1995) "Thermodynamic parameters to predict stability of RNA/DNA hybrid duplexes" Biochemistry 34:11211-11216, and et al. (1998) "Thermodynamic parameters for an expanded nearest-neighbor model for formation of RNA duplexes with Watson-Crick base pairs" Biochemistry 37: 14719-14735), R is the ideal gas constant (1.987 cal·$K^{-1}$$mole^{-1}$), and $C_t$ is the molar concentration of the oligonucleotide. The calculated $T_m$ is optionally corrected for salt concentration, e.g., $Na^+$ concentration, using the formula $1/T_m(Na^+)=1/T_m(1M)+(4.29f (G·C)−3.95)×10^{-5} \ln [Na^+]+9.40×10^{-6} \ln^2[Na^+]$. See, e.g., Owczarzy et al. (2004) "Effects of sodium ions on DNA duplex oligomers: Improved predictions of melting temperatures" Biochemistry 43:3537-3554 for further details. A web calculator for estimating Tm using the above algorithms is available on the internet at scitools.idtdna.com/analyzer/oligocalc.asp. Other algorithms for calculating Tm are known in the art and are optionally applied to the present invention.

For a given nucleic acid of interest, the corresponding target capture probes are preferably complementary to physically distinct, nonoverlapping sequences in the nucleic acid of interest, which are preferably, but not necessarily, contiguous. The $T_m$s of the individual target capture probe-nucleic acid complexes are preferably greater than the hybridization temperature, e.g., by 5° C. or 10° C. or preferably by 15° C. or more, such that these complexes are stable at the hybridization temperature. Sequence U-3 for each target capture probe is typically (but not necessarily) about 17-35 nucleotides in length, with about 30-70% GC content. Potential target capture probe sequences (e.g., potential sequences U-3) are optionally examined for possible interactions with non-corresponding nucleic acids of interest, repetitive sequences (such as polyC or polyT, for example), any detection probes used to detect the nucleic acids of interest, and/or any relevant genomic sequences, for example; sequences expected to cross-hybridize with undesired nucleic acids are typically not selected for use in the target support capture probes. Examination can be, e.g., visual (e.g., visual examination for complementarity), computational (e.g., computation and comparison of percent sequence identity and/or binding free energies; for example, sequence comparisons can be performed using BLAST software publicly available through the National Center for Biotechnology Information on the world wide web at ncbi.nlm.nih.gov), and/or experimental (e.g., cross-hybridization experiments). Support capture probe sequences are preferably similarly examined, to ensure that the polynucleotide sequence U-1 complementary to a particular support capture probe's sequence U-2 is not expected to cross-hybridize with any of the other support capture probes that are to be associated with other subsets of particles. See, e.g., Example 1 herein.

In one class of embodiments, contacting the sample, the pooled population of particles, and the subsets of n target capture probes comprises combining the sample with the subsets of n target capture probes to form a mixture, and then combining the mixture with the pooled population of particles. In this class of embodiments, the target capture probes typically hybridize first to the corresponding nucleic acid of interest and then to the corresponding particle-associated support capture probe. The hybridizations can, however, occur simultaneously or even in the opposite order. Thus, in another exemplary class of embodiments, contacting the sample, the pooled population of particles, and the subsets of n target capture probes comprises combining the sample, the subsets of target capture probes, and the pooled population of particles.

As noted, the nucleic acids are optionally detected, amplified, isolated, sequenced, and/or the like after capture. Thus, in one aspect, a plurality of the particles in each subset are distinguishable from a plurality of the particles in every other subset, and the methods include determining which subsets of particles have a nucleic acid of interest captured on the particles, thereby indicating which of the nucleic acids of interest were present in the sample. For example, in one class of embodiments, each of the nucleic acids of interest comprises a label (including, e.g., one or two or more labels per molecule), and determining which subsets of particles have a nucleic acid of interest captured on the particles comprises detecting a signal from the label. At least a portion of the particles from each subset can be identified and the presence or absence of the label detected on those particles. Since a correlation exists between a particular subset of particles and a particular nucleic acid of interest, which subsets of particles have the label present indicates which of the nucleic acids of interest were present in the sample. In one class of embodiments, the label is covalently associated with the nucleic acid. For example, a fluorescent label can be incorporated into the nucleic acid using a chemical or enzymatic labeling technique. In other embodiments, the nucleic acid is configured to bind the label; for example, a biotinylated nucleic acid can bind a streptavidin-associated label.

The label can be essentially any convenient label that directly or indirectly provides a detectable signal. In one aspect, the label is a fluorescent label (e.g., a fluorophore or quantum dot, e.g., Cy3 or Cy5). Detecting the presence of the label on the particles thus comprises detecting a fluorescent signal from the label. Fluorescent emission by the label is typically distinguishable from any fluorescent emission by the particles, e.g., microspheres, and many suitable fluorescent label-fluorescent microsphere combinations are possible. As other examples, the label can be a luminescent label, a light-scattering label (e.g., colloidal gold particles), a radioactive label, a phosphorescent label, a FRET label, or an enzyme (e.g., HRP).

The methods can optionally be used to quantitate the amounts of the nucleic acids of interest present in the sample. For example, in one class of embodiments, an intensity of the signal from the label is measured, e.g., for each subset of particles, and correlated with a quantity of the corresponding nucleic acid of interest present.

As another example, in one class of embodiments, at least one detection probe (a polynucleotide comprising a label or configured to bind a label) is provided for each nucleic acid of interest and hybridized to any nucleic acid of interest captured on the particles. As described above, determining which subsets of particles have a nucleic acid of interest captured on the particles then comprises detecting a signal from the label (e.g., a fluorescent label).

As yet another example, in one class of embodiments, determining which subsets of particles have a nucleic acid of interest captured on the particles comprises amplifying any nucleic acid of interest captured on the particles. A wide variety of techniques for amplifying nucleic acids are known in the art, including, but not limited to, PCR (polymerase chain reaction), rolling circle amplification, and transcription mediated amplification. (See, e.g., Hatch et al. (1999) "Rolling circle amplification of DNA immobilized on solid surfaces and its application to multiplex mutation detection" Genet Anal. 15:35-40; Baner et al. (1998) "Signal amplification of padlock probes by rolling circle replication" Nucleic Acids Res. 26:5073-8; and Nallur et al. (2001) "Signal amplification by rolling circle amplification on DNA microarrays" Nucleic Acids Res. 29:E118.) A labeled primer and/or labeled nucleotides are optionally incorporated during amplification. In other embodiments, the nucleic acids of interest captured on the particles are detected and/or amplified without identifying the subsets of particles and/or the nucleic acids (e.g., in embodiments in which the subsets of particles are not distinguishable).

In one class of embodiments, one or more subsets of particles is isolated, whereby any nucleic acid of interest captured on the particles is isolated. The isolated nucleic acid can optionally be removed from the particles (e.g., by eluting the nucleic acid from the particles, e.g., by heat or chemical denaturation or by selectively degrading the capture probes, optionally after washing the isolated particles to remove any unbound or non-specifically bound materials) and/or subjected to further manipulation, if desired (e.g., amplification by PCR or the like). As examples, manipulation can include enzymatic manipulation, e.g., restriction enzyme digestion, ligation, or amplification of one or more of the captured nucleic acids or a portion thereof by PCR, insertion into a vector, transformation or transfection into a host cell, determination of a polynucleotide sequence of one or more of the captured nucleic acids or a portion thereof (e.g., as described in greater detail below), and/or similar techniques well known in the art for manipulation of nucleic acids. The particles from various subsets can be distinguishable or indistinguishable.

At any of various steps, materials not captured on the particles are optionally separated from the particles. For example, after the target capture probes, nucleic acids, and particle-bound support capture probes are hybridized, the particles are optionally washed to remove unbound or non-specifically bound nucleic acids and target capture probes.

An exemplary embodiment is schematically illustrated in FIG. 1. Panel A illustrates three distinguishable subsets of microspheres 101, 102, and 103, which have associated therewith support capture probes 104, 105, and 106, respectively. Each support capture probe includes a sequence U-2 (150), which is different from subset to subset of microspheres. The three subsets of microspheres are combined to form pooled population 108 (Panel B). A subset of three target capture probes is provided for each nucleic acid of interest; subset 111 for nucleic acid 114, subset 112 for nucleic acid 115 which is not present, and subset 113 for nucleic acid 116. Each target capture probe includes sequences U-1 (151, complementary to the respective support capture probe's sequence U-2) and U-3 (152, complementary to a sequence in the corresponding nucleic acid of interest). Each nucleic acid of interest includes at least one label 117. Non-target nucleic acids 130 are also present in the sample of nucleic acids.

Nucleic acids 114 and 116 are hybridized to their corresponding subset of target capture probes (111 and 113, respectively), and the target capture probes are hybridized to the corresponding support capture probes (104 and 106, respectively), capturing nucleic acids 114 and 116 on microspheres 101 and 103, respectively (Panel C). Materials not captured on the microspheres (e.g., target capture probes 112, nucleic acids 130, etc.) are optionally separated from the microspheres by washing. Microspheres from each subset are identified, e.g., by their fluorescent emission spectrum ($\lambda_2$ and $\lambda_3$, Panel D), and the presence or absence of the label on each subset of microspheres is detected ($\lambda_1$, Panel D). Since each nucleic acid of interest is associated with a distinct subset of microspheres, the presence of the label on a given subset of microspheres correlates with the presence of the corresponding nucleic acid in the original sample.

As depicted in FIG. 1, each support capture probe typically includes a single sequence U-2 and thus hybridizes to a single target capture probe. Optionally, however, a support capture probe can include two or more sequences U-2 and hybridize to two or more target capture probes. Similarly, as depicted, each of the target capture probes in a particular subset typically includes an identical sequence U-1, and thus only a single support capture probe is needed for each subset of particles; however, different target capture probes within a subset optionally include different sequences U-1 (and thus hybridize to different sequences U-2, within a single support capture probe or different support capture probes on the surface of the corresponding subset of particles).

The methods can be used to capture the nucleic acids of interest from essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen. As additional examples, the two or more nucleic acids of interest can comprise two or more mRNAs, miRNAs, siRNAs, mitochondrial DNAs, bacterial and/or viral genomic RNAs and/or DNAs (double-stranded or single-stranded), plasmid or other extra-genomic DNAs, or other nucleic acids derived from microorganisms (pathogenic or otherwise). As described below, the nucleic acids can be longer than those readily captured by other techniques. The nucleic acids can be purified, partially purified, or unpurified. The nucleic acids are optionally, but not necessarily, produced by an amplification reaction (e.g., the nucleic acids can be the products of reverse transcription or PCR) or other genomic DNA preparation method. It will be evident that double-stranded nucleic acids of interest will typically be denatured before hybridization with target capture probes.

Due to cooperative hybridization of multiple target capture probes to a nucleic acid of interest, for example, even nucleic acids present at low concentration can be captured. Thus, in one class of embodiments, at least one of the nucleic acids of interest is present in the sample in a non-zero amount of 200 attomole (amol) or less, 150 amol or less, 100 amol or less, 50 amol or less, 10 amol or less, 1 amol or less, or even 0.1 amol or less, 0.01 amol or less, 0.001 amol or less, or 0.0001 amol or less. Similarly, two nucleic acids of interest can be captured simultaneously, even when they differ in concentration by 1000-fold or more in the sample. The methods are thus extremely versatile.

Capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured on a first subset of particles, while the second nucleic acid comprises 1% or less of a total amount of nucleic acid captured on the first subset of particles (e.g., 0.5% or less, 0.2% or less, or even 0.1% or less). The second nucleic acid can be another nucleic acid of interest or simply any nucleic acid. Typically, target capture probes are chosen that hybridize to regions of the first nucleic acid having the greatest sequence difference from the second nucleic acid.

As just one example of how closely related nucleic acids can be differentially captured using the methods of the invention, different splice variants of a given mRNA can be selectively captured. Thus, in one class of embodiments, the sample comprises a first nucleic acid of interest and a second nucleic acid, where the first nucleic acid is a first splice variant and the second nucleic acid is a second splice variant of the given mRNA. A first subset of n target capture probes is capable of hybridizing to the first splice variant, of which at most n−1 target capture probes are capable of hybridizing to the second splice variant. Optionally, at least 80% or more, 90% or more, or 95% or more of the first splice variant is captured on a first subset of particles while at most 10% or less, 5% or less, 3% or less, or 1% or less of the second splice variant is captured on the first subset of particles.

Preferably, hybridization of the n target capture probes to the first splice variant captures the first splice variant on a first subset of particles while hybridization of the at most n–1 target capture probes to the second splice variant does not capture the second splice variant on the first subset of particles. An exemplary embodiment illustrating capture of two splice variants is schematically depicted in FIG. 2. In this example, three target capture probes 211 hybridize to first splice variant 221, one to each exon (224 and 226) and one to splice junction 227 (the only sequence found in first splice variant 221 and not also found in second splice variant 222); two of these bind to second splice variant 222. Similarly, three target capture probes 212 bind to second splice variant 222, one to intron 225 and one to each of the splice junctions; none of these bind to first splice variant 221. Through cooperative hybridization of the target capture probes to the splice variants and to the corresponding support capture probes (204 and 205), splice variants 221 and 222 are each captured specifically only on the corresponding subset of microspheres (201 and 202, respectively). Sequences (e.g., DNAs) comprising translocation event junctions can be similarly selectively captured. Optionally, for any nucleic acid, hybridization of a first subset of n target capture probes to a first nucleic acid captures the first nucleic acid on a first subset of particles while hybridization of at most n–1 of the target capture probes to a second nucleic acid does not capture the second nucleic acid on the first subset of particles.

It will be evident that nucleic acids that do not have 100% identical sequences are alternatively optionally captured on the same subset of particles, if desired. For example, a first and a second nucleic acid are optionally both captured on a first subset of particles, through binding of the same or different subsets of target capture probes. The first and second nucleic acids can be closely related; for example, splice variants of a particular mRNA, different alleles of a gene, somatic mutations, homologs, or the like. Similarly, it will be evident that a single type of particle bearing a single support capture probe (rather than multiple distinguishable subsets of particles bearing different support capture probes) can be used to capture multiple nucleic acids, e.g., in aspects in which a few specific target nucleic acids are to be isolated and/or in which individual targets need not be identified (e.g., sequencing).

A support capture probe and/or target capture probe optionally comprises at least one non-natural nucleotide. For example, a support capture probe and the corresponding target capture probe optionally comprise, at complementary positions, at least one pair of non-natural nucleotides that base pair with each other but that do not Watson-Crick base pair with the bases typical to biological DNA or RNA (i.e., A, C, G, T, or U). Examples of nonnatural nucleotides include, but are not limited to, Locked NucleicAcid™ nucleotides (available from Exiqon A/S, on the world wide web at www (dot) exiqon (dot) com), isoG, isoC, and other nucleotides used in the AEGIS system (Artificially Expanded Genetic Information System, available from Era-Gen Biosciences, www (dot) eragen (dot) com), and constrained ethyl analogs such as those available from Isis; see, e.g., SantaLucia Jr. (1998) Proc Natl Acad Sci 95:1460-1465, U.S. Pat. Nos. 6,001,983, 6,037,120, 6,140,496, 7,572,582, 6,670,461, 6,794,499, 7,034,133, 5,700,637, 5,436,327, and 7,399,846. Use of such conformationally constrained bases or non-natural base pairs (e.g., isoG-isoC base pairs) in the support capture probes and target capture probes can, for example, decrease cross hybridization, or it can permit use of shorter support capture probe and target capture probes when the non-natural base pairs have higher binding affinities than do natural base pairs.

The preceding embodiments include capture of the nucleic acids of interest on particles. Alternatively, the nucleic acids can be captured at different positions on a non-particulate, spatially addressable solid support. Accordingly, another general class of embodiments includes methods of capturing two or more nucleic acids of interest. In the methods, a sample, a solid support, and two or more subsets of n target capture probes, wherein n is at least two, are provided. The sample comprises or is suspected of comprising the nucleic acids of interest. The solid support comprises two or more support capture probes, each of which is provided at a selected position on the solid support. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support. Each nucleic acid of interest can thus, by hybridizing to its corresponding subset of n target capture probes which are in turn hybridized to a corresponding support capture probe, be associated with, e.g., a known, predetermined location on the solid support. The sample, the solid support, and the subsets of n target capture probes are contacted, any nucleic acid of interest present in the sample is hybridized to its corresponding subset of n target capture probes, and the subset of n target capture probes is hybridized to its corresponding support capture probe. The hybridizing the nucleic acid of interest to the n target capture probes and the n target capture probes to the corresponding support capture probe captures the nucleic acid on the solid support at the selected position with which the target capture probes are associated.

The hybridizing the subset of n target capture probes to the corresponding support capture probe is typically performed at a hybridization temperature which is greater than a melting temperature $T_m$ of a complex between each individual target capture probe and its corresponding support capture probe. For example, the hybridization temperature can be about 5° C. or more greater than the $T_m$, e.g., about 7° C. or more, about 10° C. or more, about 12° C. or more, about 15° C. or more, about 17° C. or more, or even about 20° C. or more greater than the $T_m$.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, 100 or more, $10^3$ or more, or $10^4$ or more nucleic acids of interest. A like number of selected positions on the solid support and subsets of target capture probes are provided; thus, the two or more selected positions can comprise five or more, 10 or more, 20 or more, 30 or more, 40 or more, 50 or more, 100 or more, $10^3$ or more, or $10^4$ or more selected positions, while the two or more subsets of n target capture probes can comprise five or more, 10 or more, 20 or more, 30 or more, 40 or more, 50 or more, 100 or more, $10^3$ or more, or $10^4$ or more subsets of n target capture probes.

The solid support typically has a planar surface and is typically rigid, but essentially any spatially addressable solid support of any shape, size, etc. can be adapted to the practice of the present invention. Exemplary materials for the solid support include, but are not limited to, glass, silicon, silica, quartz, plastic, polystyrene, nylon, and nitrocellulose. As just one example, an array of support capture probes can be formed at selected positions on a glass slide as the solid support.

As for the embodiments described above, the nucleic acids are optionally detected, amplified, isolated, manipulated, and/or the like after capture. Thus, in one aspect, the methods include determining which positions on the solid support have a nucleic acid of interest captured at that position, thereby indicating which of the nucleic acids of interest were present in the sample. For example, in one class of embodiments, each of the nucleic acids of interest comprises a label (including, e.g., one or two or more labels per molecule), and determining which positions on the solid support have a nucleic acid of interest captured at that position comprises detecting a signal from the label, e.g., at each position. Since a correlation exists between a particular position on the support and a particular nucleic acid of interest, which positions have a label present indicates which of the nucleic acids of interest were present in the sample. In one class of embodiments, the label is covalently associated with the nucleic acid. In other embodiments, the nucleic acid is configured to bind the label; for example, a biotinylated nucleic acid can bind a streptavidin-associated label.

The methods can optionally be used to quantitate the amounts of the nucleic acids of interest present in the sample. For example, in one class of embodiments, an intensity of the signal from the label is measured, e.g., for each of the selected positions, and correlated with a quantity of the corresponding nucleic acid of interest present.

As another example, in one class of embodiments, at least one detection probe (a polynucleotide comprising a label or configured to bind a label) is provided for each nucleic acid of interest and hybridized to any nucleic acid of interest captured on the support. As described above, determining which positions on the support have a nucleic acid of interest captured on the support then comprises detecting a signal from the label. As yet another example, in one class of embodiments, determining which positions on the solid support have a nucleic acid of interest captured at that position comprises amplifying any nucleic acid of interest captured on the solid support, as for the embodiments described above.

At any of various steps, materials not captured on the solid support are optionally separated from the solid support. For example, after the target capture probes, nucleic acids, and support-bound support capture probes are hybridized, the solid support is optionally washed to remove unbound nucleic acids and target capture probes.

Essentially all of the features noted for the methods above apply to these embodiments as well, as relevant; for example, with respect to number of target capture probes per subset, configuration of the target capture probes and/or support capture probes, type of particles, label configuration, source of the sample and/or nucleic acids, and/or the like.

For example, in one class of embodiments, contacting the sample, the solid support, and the subsets of n target capture probes comprises combining the sample with the subsets of n target capture probes to form a mixture, and then contacting the mixture with the solid support. In this class of embodiments, the target capture probes typically hybridize first to the corresponding nucleic acid of interest and then to the corresponding particle-associated support capture probe. In other embodiments, however, the hybridizations can occur simultaneously or even in the opposite order.

As for the embodiments described above, capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured at a first selected position on the solid support. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured at a first selected position on the solid support, while the second nucleic acid comprises 1% or less of a total amount of nucleic acid captured at the first position (e.g., 0.5% or less, 0.2% or less, or even 0.1% or less). The second nucleic acid can be another nucleic acid of interest or simply any nucleic acid. Typically, target capture probes are chosen that hybridize to regions of the first nucleic acid having the greatest sequence difference from the second nucleic acid.

As just one example of how closely related nucleic acids can be differentially captured using the methods of the invention, different splice variants of a given mRNA can be selectively captured. Thus, in one class of embodiments, the sample comprises a first nucleic acid of interest and a second nucleic acid, where the first nucleic acid is a first splice variant and the second nucleic acid is a second splice variant of the given mRNA. A first subset of n target capture probes is capable of hybridizing to the first splice variant, of which at most n−1 target capture probes are capable of hybridizing to the second splice variant. Optionally, at least 80% or more, 90% or more, or 95% or more of the first splice variant is captured at a first selected position on the solid support while at most 10% or less, 5% or less, 3% or less, or 1% or less of the second splice variant is captured at the first position. Preferably, hybridization of the n target capture probes to the first splice variant captures the first splice variant at a first selected position on the solid support while hybridization of the at most n−1 target capture probes to the second splice variant does not capture the second splice variant at the first position.

It will be evident that nucleic acids that do not have 100% identical sequences are alternatively optionally captured at the same position of the support, if desired. For example, a first and a second nucleic acid are optionally both captured at a first position, through binding of the same or different subsets of target capture probes. The first and second nucleic acids can be closely related; for example, splice variants of a particular mRNA, different alleles of a gene, somatic mutations, homologs, or the like. Similarly, it will be evident that a single support-bound support capture probe (rather than different support capture probes at different selected positions on the support) can be used to capture multiple nucleic acids, e.g., in aspects in which a few specific target nucleic acids are to be isolated and/or in which individual targets need not be identified.

Figure 3:
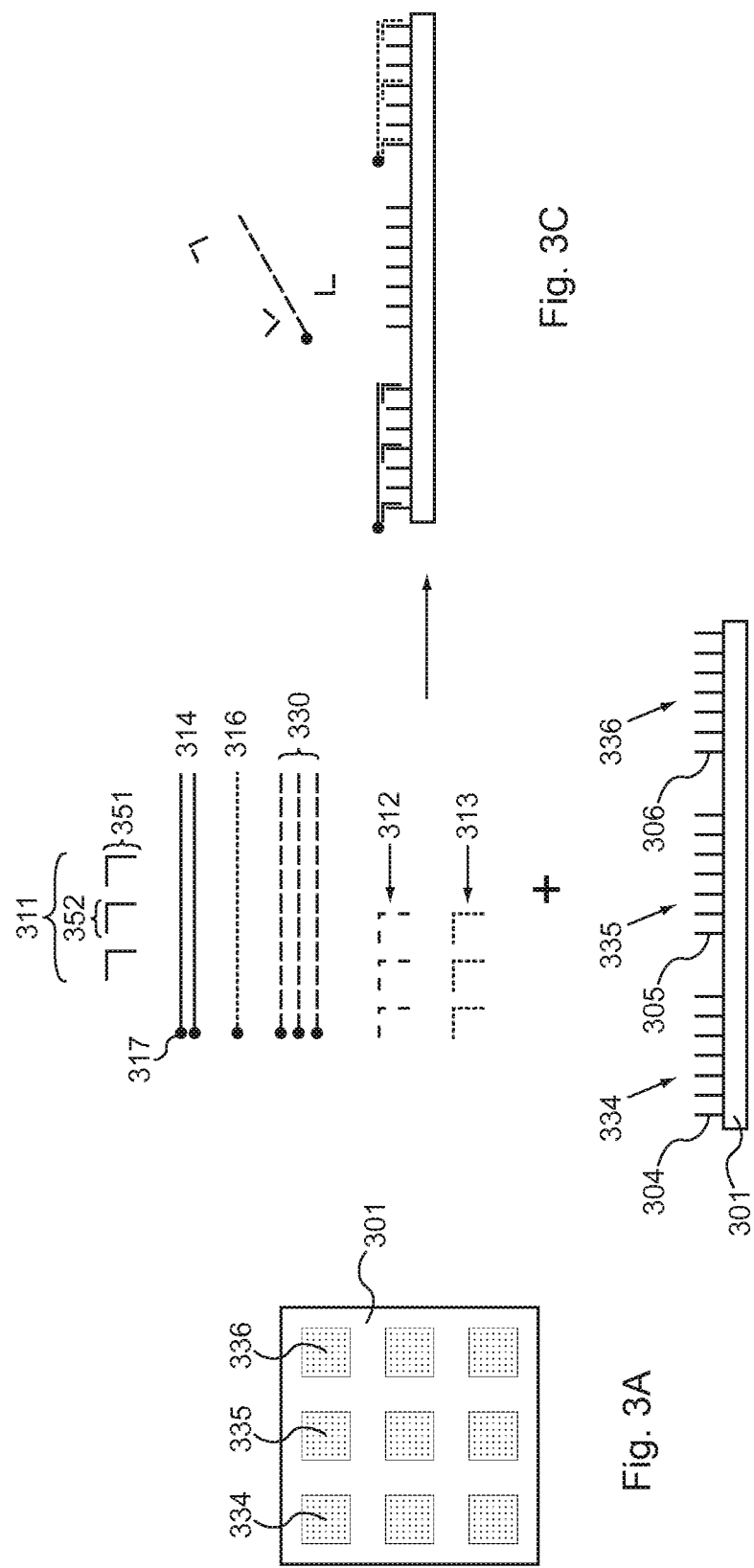
FIG. 3 Panels A-C schematically depict multiplex capture of nucleic acids, where the nucleic acids of interest are captured at selected positions on a solid support. Panel A shows a top view of the solid support, while Panels B-C show the support in cross-section.

An exemplary embodiment is schematically illustrated in FIG. 3. Panel A depicts solid support 301 having nine support capture probes provided on it at nine selected positions (e.g., 334-336). Panel B depicts a cross section of solid support 301, with distinct support capture probes 304, 305, and 306 at different selected positions on the support (334, 335, and 336, respectively). A subset of target capture probes is provided for each nucleic acid of interest. Only three subsets are depicted; subset 311 for nucleic acid 314, subset 312 for nucleic acid 315 which is not present, and subset 313 for nucleic acid 316. Each target capture probe includes sequences U-1 (351, complementary to the respective support capture probe's sequence U-2) and U-3 (352, complementary to a sequence in the corresponding nucleic acid of interest). Each nucleic acid of interest includes at least one label 317. Non-target nucleic acids 330 are also present in the sample of nucleic acids.

Nucleic acids 314 and 316 are hybridized to their corresponding subset of target capture probes (311 and 313, respectively), and the target capture probes are hybridized to the corresponding support capture probes (304 and 306, respectively), capturing nucleic acids 314 and 316 at selected positions 334 and 336, respectively (Panel C). Materials not captured on the solid support (e.g., target capture probes 312, nucleic acids 330, etc.) are optionally removed by washing the support, and the presence or absence of the label at each position on the solid support is detected. Since each nucleic acid of interest is associated with a distinct position on the support, the presence of the label at a given position on the support correlates with the presence of the corresponding nucleic acid in the original sample.

As noted above, in some aspects multiple nucleic acids can be captured collectively through binding to a single support capture probe. This can be useful, for example, in embodiments where identification of the individual nucleic acids is not required, e.g., where the nucleic acids are subsequently sequenced. Accordingly, another general class of embodiments provides methods of capturing two or more nucleic acids of interest, generally different nucleic acids. In the methods, a sample, a solid support, and two or more subsets of n target capture probes (typically n different target capture probes), wherein n is at least two, are provided. The sample comprises or is suspected of comprising the nucleic acids of interest. A support capture probe is associated with the solid support. A different subset of target capture probes is provided for each different nucleic acid of interest. The target capture probes in each subset are capable of hybridizing to nonoverlapping polynucleotide sequences in the corresponding nucleic acid of interest. The target capture probes in each subset are also capable of hybridizing to the support capture probe.

Any nucleic acid of interest present in the sample is hybridized to its corresponding subset of n target capture probes, and the subset of n target capture probes is hybridized to the support capture probe, thereby capturing the nucleic acid on the solid support. The hybridizing the subset of n target capture probes to the support capture probe is performed at a hybridization temperature which is greater than a melting temperature $T_m$ of a complex between each individual target capture probe and the support capture probe.

In some embodiments, for example, where the different nucleic acids are to be separately isolated or detected, different nucleic acids are captured via different support capture probes to different distinguishable subsets of particles or to different preselected positions on a spatially addressable solid support, as detailed above. In other embodiments, for example, where individual targets need not be identified (e.g., where the different nucleic acids are to be processed simultaneously after their capture), the different nucleic acids are captured to a single solid support through binding of their target capture probes to a single type of support capture probe. Thus, in one class of embodiments, the solid support comprises particles of a single type, which particles bear the support capture probe. The particles optionally have additional desirable characteristics. For example, the particles can be magnetic, diamagnetic, superparamagnetic, or paramagnetic, which provides a convenient means for separating the particles from solution, e.g., to simplify separation of the particles from any materials not bound to the particles. The particles are optionally detectable, e.g., fluorescent. In another class of embodiments, the solid support comprises a surface of a well of a multiwell plate bearing the support capture probe.

The nucleic acids can be removed from the solid support after their capture, e.g., after washing the support to remove any unbound nucleic acids. Target capture probes are optionally separated from the captured nucleic acids. Removal of the target capture probes from the captured nucleic acids can be desirable, for example, in applications where the nucleic acids are subsequently subjected to manipulation such as ligation to oligonucleotide adapters, primer-dependent enzymatic amplification, or the like. In one class of embodiments, the target capture probes are separated from the captured nucleic acids based on their relative sizes, e.g., by gel or capillary electrophoresis, affinity binding (e.g., to a silica membrane or particles), ultrafiltration, or similar techniques. In a related class of embodiments, the target capture probes are selectively degraded. Any of a variety of techniques that selectively remove the target capture probes while leaving the nucleic acids of interest intact can be employed. For example, the target capture probes can include RNA nucleotides that are digested by ribonuclease, phosphorothiolate linkages cleaved by silver ions, or internucleosidic phosphoramidates cleaved by acid. In yet another class of embodiments, the target capture probes can be tagged and removed by affinity purification; for example, biotinylated target capture probes (e.g., biotinylated RNA probes) can be conveniently removed through binding to avidin or streptavidin.

The captured nucleic acids can be manipulated, optionally after their removal from the solid support and/or separation from the target capture probes. Manipulation can include enzymatic manipulation, e.g., restriction enzyme digestion, ligation, or amplification of one or more of the captured nucleic acids or a portion thereof by PCR, insertion into a vector, transformation or transfection into a host cell, and/or similar techniques well known in the art for manipulation of nucleic acids. In one exemplary class of embodiments, a polynucleotide sequence of one or more of the captured nucleic acids or a portion thereof is determined. Essentially any technique can be employed for determining the polynucleotide sequence, including, but not limited to, sequencing by synthesis, sequencing by cyclic reversible termination, sequencing by single nucleotide addition, real-time sequencing, dideoxy sequencing, sequencing by ligation, sequencing by hybridization, single molecule sequencing, or nanopore sequencing. As discussed in greater detail hereinbelow, the methods are useful for performing a chromosome walk, capturing desired targets for resequencing, or for capturing nucleic acids of particular interest for sequencing (e.g., members of the gene or protein family, nucleic acids including a conserved motif, genes implicated in a disease process or in response to treatment, etc.).

Essentially any type (or combination of types) of nucleic acids can be captured using the methods of the invention. For example, in one class of embodiments the two or more different nucleic acids of interest are two or more different DNAs, e.g., two or more different fragments of genomic or mitochondrial DNA. The DNA fragments can be overlapping, contiguous, non-contiguous, or even derived from two or more different sources. Optionally, the nucleic acids of interest include two or more sets of genomic DNA fragments, overlapping within and optionally but not necessarily between sets, where the fragments in each set include a region that is complementary to one of the subsets of target capture probes; different sets of fragments include different regions complementary to different subsets of the target capture probes. In another class of embodiments, the two or more different nucleic acids of interest are two or more different RNAs. Optionally, the two or more different nucleic acids of interest represent two or more different exons. Similarly, the two or more different nucleic acids of interest can represent two or more different introns. Additional exemplary nucleic acids include, but are not limited to, miRNAs, siRNAs, and mitochondrial DNAs.

Similarly, the nucleic acids can be of varying lengths, including lengths greater than those generally captured by current techniques. Thus, in one class of embodiments, at least one of the nucleic acids of interest is at least 20 kilobases in length, e.g., at least 50 kilobases, at least 100 kilobases, at least 250 kilobases, or at least 500 kilobases in length.

A captured nucleic acid can be detected and optionally quantitated, e.g., by incorporation of a label into the nucleic acid, binding of a detection probe, amplification, or the like, as described above.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, or even 100 or more nucleic acids of interest. A like number of subsets of target capture probes is typically provided; thus, the two or more subsets of n target capture probes can comprise five or more, 10 or more, 20 or more, 30 or more, 40 or more, 50 or more, or even 100 or more subsets of n target capture probes.

As noted, each of the two or more subsets of target capture probes includes n target capture probes, where n is at least two. Preferably, n is at least three, and n can be at least four or at least five or more. Typically, but not necessarily, n is at most ten.

Each target capture probe is capable of hybridizing to the support capture probe. The target capture probe typically includes a polynucleotide sequence U-1 that is complementary to a polynucleotide sequence U-2 in the support capture probe. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive).

As noted, the hybridizing the subset of n target capture probes to the support capture probe is performed at a hybridization temperature which is greater than a melting temperature $T_m$ of a complex between each individual target capture probe and the support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$. Hybridization of the target capture probes to the nucleic acids of interest and to the support capture probe can occur simultaneously or in either order.

At any of various steps, materials not captured on the solid support are optionally separated from the support. For example, after the target capture probes, nucleic acids, and support-bound support capture probe are hybridized, the solid support is optionally washed to remove unbound nucleic acids and target capture probes.

The methods can be used to capture the nucleic acids of interest from essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen.

The methods of the present invention offer a number of advantages. For example, a single array of support capture probes at selected positions on a solid support can be manufactured, and this single array can be used to capture essentially any desired group of nucleic acids of interest simply by synthesizing appropriate subsets of target capture probes. A new array need not be manufactured for each new group of nucleic acids to be captured, unlike conventional microarray technologies in which arrays of target-specific probes attached to a solid support are utilized, necessitating the manufacture of a new array for each new group of target nucleic acids to be captured and detected. Similarly, a single population of subsets of particles comprising support capture probes can be manufactured and used for capture of essentially any desired group of nucleic acids of interest. Nucleic acids can be easily captured and purified from even complex samples for subsequent processing such as polynucleotide sequencing. As previously noted, capture of a nucleic acid of interest through multiple, individually relatively weak hybridization events can provide greater specificity than does capturing the nucleic acid through hybridization with a single oligonucleotide. It can also provide greater ability to discriminate between closely related sequences than does capturing the nucleic acid through hybridization with a cDNA or other large probe.

Capture of Long Nucleic Acids

Capture of nucleic acids through cooperative hybridization of multiple target capture probes to each nucleic acid can facilitate capture of nucleic acids that are longer than those readily accessible through other capture techniques, particularly techniques used to capture nucleic acids for subsequent polynucleotide sequence determination. For example, the NimbleGen capture arrays commercially available from Roche NimbleGen, Inc. (www dot nimblegen dot com) are designed for capture of fragments that are approximately 500 nucleotides in length. Genomic DNA intended for capture on the NimbleGen arrays may initially be at least 12 kilobases in length, but is fragmented by nebulization or sonication prior to capture on the array. In addition, capture of targets through hybridization to NimbleGen arrays may lead to unintended bias in the nucleic acids recovered; see, e.g., Hoppman-Chaney et al. (2010) "Evaluation of Oligonucleotide Sequence Capture Arrays and Comparison of Next-Generation Sequencing Platforms for Use in Molecular Diagnostics" Clinical Chemistry 56: 1297-1306, which describes difficulty in enriching GC-rich regions. Capture through cooperative hybridization as described herein may also permit use of smaller quantities of nucleic acid, since losses to nebulization or sonication need not be incurred.

Furthermore, capture through cooperative hybridization is efficient and typically avoids any need for pre-purification of samples or for enzymatic amplification of the targets.

Accordingly, one general class of embodiments includes methods of capturing long nucleic acids. In the methods, a sample, a solid support, and one or more subset of n target capture probes (typically n different target capture probes), wherein n is at least two, are provided. The sample comprises or is suspected of comprising one or more nucleic acid of interest, which nucleic acid is at least 20 kilobases in length. The solid support comprises a support capture probe associated with the support. The target capture probes in each subset are capable of hybridizing to nonoverlapping polynucleotide sequences in the corresponding nucleic acid of interest, and the target capture probes in each subset are also capable of hybridizing to the support capture probe. Any nucleic acid of interest present in the sample is hybridized to its corresponding subset of n target capture probes, and the subset of n target capture probes is hybridized to the support capture probe, thereby capturing the nucleic acid on the solid support. Hybridizing the subset of n target capture probes to the support capture probe is performed at a hybridization temperature which is greater than a melting temperature $T_m$ of a complex between each individual target capture probe and the support capture probe.

The one or more nucleic acid of interest can be, e.g., 20-30 kilobases in length, 30-40 kilobases in length, 40-50 kilobases in length, 50-75 kilobases in length, or 75-100 kilobases in length. As additional examples, the one or more nucleic acid of interest can be, e.g., at least 35 kilobases in length, at least 50 kilobases in length, at least 75 kilobases in length, at least 100 kilobases in length, at least 250 kilobases in length, or even at least 500 kilobases in length. Despite the length of the nucleic acid to be captured, the target capture probes are optionally clustered within a small region of the nucleic acid. For example, the subset of n target capture probes optionally hybridizes within a region of the corresponding nucleic acid of interest that is less than 1000 bases, e.g., less than 750 bases, less than 600 bases, or less than 500 bases in length. In other embodiments, the target capture probes can be equally distributed along the entire length of the nucleic acid of interest, clustered in two groups with one group at each of the two ends of the nucleic acid of interest, or otherwise randomly spread throughout the target. Optionally, the target capture probes may be designed to hybridize to one or more regions within the target that are determined to be optimal for sensitivity and specificity.

As for the embodiments described above, the solid support can be essentially any suitable support, including, but not limited to, various particles as described above (e.g., a single type of particles bearing a single support capture probe or two or more subsets of distinguishable particles bearing different support capture probes), a spatially addressable solid support bearing different support capture probes at different predetermined positions on the support, a surface of a well of a multiwell plate, or a combination thereof.

Essentially any type of long nucleic acid can be captured using the methods, including, e.g., DNA, e.g., one or more fragments of genomic or mitochondrial DNA. The DNA fragments can be overlapping, contiguous, non-contiguous, or even derived from two or more different sources. Thus, in one exemplary class of embodiments, the one or more nucleic acid of interest comprises at least two overlapping fragments of genomic DNA, which overlapping fragments each include a region complementary to the n target capture probes. Optionally, the nucleic acids of interest include two or more sets of genomic DNA fragments (typically overlapping within but not necessarily between the sets), where each set includes a different region complementary to a different set of n target capture probes.

It will be evident that careful treatment of the starting sample is desirable to maintain the desired length of the target nucleic acids. For example, enzymatic and/or osmotic lysis will typically be preferred to mechanical lysis to avoid shearing genomic DNA. For example, a hypotonic gentle lysis buffer containing a detergent and/or protease digestion can be employed.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, label configuration, source of the sample and/or nucleic acids, hybridization temperature, subsequent isolation or manipulation of the nucleic acids, and/or the like. For example, the methods can include determining a polynucleotide sequence of the captured nucleic acid or a portion thereof.

Capture of exemplary human genomic DNA fragments at least about 35 kilobases in length is described below, in Example 2.

Applications to Polynucleotide Sequencing

Capture of nucleic acids through cooperative hybridization is a useful means of purifying them for subsequent polynucleotide sequence determination. Accordingly, one general class of embodiments provides methods of sequencing one or more nucleic acids of interest. In the methods, a sample, a solid support, and one or more subsets of n target capture probes (typically n different target capture probes), wherein n is at least two, are provided. The sample comprises or is suspected of comprising the one or more nucleic acids of interest. A support capture probe is associated with the solid support.

As noted, one or more subsets of target capture probes is provided, e.g., a different subset for each different nucleic acid of interest or for each different set of overlapping nucleic acids, where each set includes a region complementary to one subset of the target capture probes. The target capture probes in each subset are capable of hybridizing to nonoverlapping polynucleotide sequences in the corresponding nucleic acid of interest. The target capture probes in each subset are also capable of hybridizing to the support capture probe.

For each of the nucleic acids of interest, the nucleic acid is hybridized to its corresponding subset of n target capture probes, and the subset of n target capture probes is hybridized to the support capture probe, thereby capturing the nucleic acid on the solid support. The hybridizing the subset of n target capture probes to the support capture probe is performed at a hybridization temperature which is greater than a melting temperature $T_m$ of a complex between each individual target capture probe and the support capture probe. A polynucleotide sequence of the captured nucleic acids or a portion thereof is determined.

Suitable solid supports are well known in the art. Optionally, different nucleic acids (or different sets of nucleic acids that include a common region complementary to a subset of target capture probes) are captured to different distinguishable subsets of particles or to different preselected positions on a spatially addressable solid support as described herein. Typically, however, the nucleic acids of interest are processed simultaneously after their capture and can thus be captured collectively. Accordingly, different nucleic acids are optionally captured to a single solid support through binding of their target capture probes to a single type of support capture probe. For example, in one class of embodiments, the solid support comprises particles of a single type, which particles bear the support capture probe. The particles can be magnetic, diamagnetic, superparamagnetic, or paramagnetic, which provides a convenient means for separating the particles from solution, e.g., to simplify separation of the particles from any materials not bound to the particles. In another class of embodiments, the solid support comprises a surface of a well of a multiwell plate bearing the support capture probe.

The nucleic acids can be removed from the solid support after their capture, e.g., by denaturation, e.g., after washing the support to remove any unbound nucleic acids. Target capture probes are optionally separated from the captured nucleic acids, e.g., after their removal from the support. Removal of the target capture probes from the captured nucleic acids can be desirable, for example, in applications where the nucleic acids are subsequently subjected to manipulation such as ligation to oligonucleotide adapters, primer-dependent enzymatic amplification, or the like, or to ensure that the target capture probes do not interfere with the sequencing reaction. In one class of embodiments, the target capture probes are separated from the captured nucleic acids based on their relative sizes, e.g., by gel or capillary electrophoresis, affinity binding (e.g., to a silica membrane or particles), ultrafiltration, or similar techniques. In a related class of embodiments, the target capture probes are selectively degraded. Any of a variety of techniques that selectively remove the target capture probes while leaving the nucleic acids of interest intact can be employed. For example, the target capture probes can include RNA nucleotides that are digested by ribonuclease, phosphorothiolate linkages cleaved by silver ions, or internucleosidic phosphoramidates cleaved by acid. In yet another class of embodiments, the target capture probes can be tagged and removed by affinity purification; for example, biotinylated target capture probes (e.g., biotinylated RNA probes) can be conveniently removed through binding to avidin or streptavidin. In other embodiments, the target capture probes are not removed from the captured nucleic acids (e.g., in applications where adaptors, primers, or the like are provided in excess).

The captured nucleic acids can but need not be manipulated, optionally after their removal from the solid support and/or separation from the target capture probes, prior to sequencing. Such manipulation can include enzymatic manipulation, e.g., restriction enzyme digestion, ligation (e.g., to oligonucleotide adapters), or amplification of one or more of the captured nucleic acids or a portion thereof by PCR, insertion into a vector, transformation or transfection into a host cell, labeling, and/or similar techniques well known in the art for manipulation of nucleic acids.

Essentially any technique can be employed for determining the polynucleotide sequence, including, but not limited to, sequencing by synthesis, sequencing by cyclic reversible termination, sequencing by single nucleotide addition, real-time sequencing, dideoxy sequencing, sequencing by ligation, sequencing by hybridization, single molecule sequencing, or nanopore sequencing. A variety of such techniques for polynucleotide sequencing that can be adapted to the practice of the present invention are well known in the art. For example, for information on dideoxy (Sanger) or Maxam-Gilbert sequencing, see, e.g., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., Current Protocols, a joint venture between Greene Publishing Associates, Inc. and John Wiley & Sons, Inc. (supplemented through 2010). Various next-generation sequencing techniques are reviewed, e.g., in Metzker (2010) "Sequencing technologies—The next generation" Nature Reviews Genetics 11:31-46, Voelkerding et al. (2009) "Next-generation sequencing: From basic research to diagnostics" Clin Chem 55:641-658, Dhiman et al. (2009) "Next-generation sequencing: A transformative tool for vaccinology" Expert Rev Vaccines 8:963-967, and Turner et al. (2009) "Next-generation sequencing of vertebrate experimental organisms" Mamm Genome 20:327-338. Nanopore sequencing is reviewed, e.g., in Branton et al. (2008) "The potential and challenges or nanopore sequencing" Nature Biotech 26:1146-1153. Furthermore, equipment and reagents for sequencing are commercially available from a large number of suppliers. Exemplary commercial suppliers of next-generation sequencing systems and reagents include Roche/454 (454 sequencing system, 454 dot com), Illumina (e.g., Solexa Genome Analyzer, www dot illumina dot com), Applied Biosystems (SOLiD™ system, www dot appliedbiosystems dot com), Helicos BioSciences (HeliScope, www dot helicosbio dot com), and Pacific Biosciences (PacBio RS and SMRT sequencing, www dot pacificbiosciences dot com).

By facilitating specific capture of desired nucleic acids for sequencing, the cooperative hybridization capture techniques described herein are useful for a large number of sequencing applications. A few examples follow, but more will be evident to one of skill based on the disclosure herein. The techniques can be employed for de novo sequencing: sequence information from one region is readily extended in either or both directions by designing target capture probes from the 3' and/or 5' ends of the known sequence, using these target capture probes to capture fragments overlapping the initial region but extending further 3' or 5', sequencing those fragments, and repeating the design, capture, and sequencing steps as needed, e.g., to perform a chromosome walk (similar to those traditionally performed using overlapping clones; see, e.g., Griffiths et al. (2007) Introduction to Genetic Analysis, Ninth Edition, W. H. Freeman). The capture methods described herein are also particularly suited for capturing desired targets for resequencing, e.g., of genomic subregions, gene sets, or the like, for applications such as detection of polymorphisms and mutations. For example, the same chromosome or region can be captured and sequenced from different species, strains, or individuals. Generally, the methods are useful for capturing essentially any nucleic acids of particular interest for sequencing (e.g., a subset of a genomic sample, members of a gene or protein family, nucleic acids including a conserved motif, all exons or a subset thereof, all introns or a subset thereof, all transcription factor transcripts, genes implicated in a disease process or in response to treatment, etc.).

For example, the methods can be employed to capture families of nucleic acids which have a common target sequence, such as a common motif in a family of enzymes, receptors, signal transduction and signaling proteins, transcription factors, structural proteins, adhesion molecules, chromatin components, or the like. A large number of such sequences and motifs are known in the art. See, e.g., Aitken (1999) "Protein consensus sequence motifs" Mol Biotechnol. 12(3):241-53, Yaffe and Elia (2001) "Phosphoserine/threonine-binding domains" Curr Opin Cell Biol. 13(2):131-8, Li et al. (2000) "The FHA domain mediates phosphoprotein interactions" J Cell Sci. 113 Pt 23:4143-9, Chothia (1992) "Proteins. One thousand families for the molecular biologist" Nature 357(6379):543-4, and Das and Smith (2000) "Identifying nature's protein Lego set" Adv Protein Chem. 54:159-83. Examples include, but are not limited to, phosphorylation site motifs for protein kinases, metal binding sites (e.g., for calcium, zinc, copper, and iron), enzyme active site motifs, nucleotide binding sites, covalent attachment sites for prosthetic groups, carbohydrates, and lipids, sequences that target proteins to particular subcellular locations, cell-signaling motifs, and protein-protein interaction motifs such as 14-3-3, ADF, ANK, ARM, BAR, BEACH, BH 1-4, BIR, BRCT, BROMO, BTB, C1, C2, CARD, CC, CALM, CH, Chr, CUE, DD, DED, DH, EF-hand, EH, ENTH, EVH1, F-box, FERM, FF, FH2, FHA, FYVE, GAT, GEL, GLUE, GRAM, GRIP, GYF, HEAT, HECT, IQ, LIM, LRR, MBT, MH1, MH2, MIU, NZF, PAS, PB1, PDZ, PH, Polo-Box, PTB, PUF, PWWP, PX, RGS, RING, SAM, SC, SH2, SH3, SOCS, SPRY, START, SWIRM, TIR, TPR, TRAF, tSNARE, TUBBY, TUDOR, UBA, UEV, UIM, VHLβ, VHS, WD40, and WW domains.

Essentially any type (or combination of types) of nucleic acids can be isolated and sequenced using the methods of the invention. For example, in one class of embodiments the one or more nucleic acids of interest are one or more DNAs, e.g., one or more fragments of genomic or mitochondrial DNA. Where two or more fragments of DNA are captured and sequenced, the DNA fragments can be overlapping, contiguous, non-contiguous, or even derived from two or more different sources. Thus, in one exemplary class of embodiments, the one or more nucleic acid of interest comprises at least two overlapping fragments of genomic DNA, which overlapping fragments each include a region complementary to the n target capture probes. Optionally, the nucleic acids of interest include two or more sets of genomic DNA fragments (typically overlapping within but not necessarily between the sets), where each set includes a different region complementary to a different set of n target capture probes. In another class of embodiments, the two or more different nucleic acids of interest are two or more different RNAs. Optionally, the one or more nucleic acids of interest comprise two or more different nucleic acids of interest, which two or more different nucleic acids of interest represent two or more different exons. Similarly, the two or more different nucleic acids of interest can represent two or more different introns.

As noted, multiple nucleic acids can be captured simultaneously for sequencing. Thus, the one or more nucleic acids of interest optionally comprise two or more, five or more, 10 or more, 20 or more, 30 or more, 40 or more, 50 or more, or even 100 or more nucleic acids of interest. A like number of subsets of target capture probes is typically provided; thus, the one or more subsets of n target capture probes can comprise two or more, five or more, 10 or more, 20 or more, 30 or more, 40 or more, 50 or more, or even 100 or more subsets of n target capture probes. An additional degree of multiplexing is optionally achieved as described in U.S. patent publication 2009/0131269 by Jason Martin, et al., "Highly Multiplexed Particle-Based Assays." As just one example, when capture is achieved on the surface of wells or on beads contained in wells of a multiwell plate, a single 96 well plate can provide sequence information from a large part of a genome or total sequence information for a single or for multiple chromosomes.

As for the embodiments above, the nucleic acids can be of varying lengths, including lengths greater than those generally captured by current techniques. Thus, in one class of embodiments, at least one of the nucleic acids of interest is at least 20 kilobases in length, e.g., at least 50 kilobases, at least 100 kilobases, at least 250 kilobases, or at least 500 kilobases in length.

As noted, each of the two or more subsets of target capture probes includes n target capture probes, where n is at least two. Preferably, n is at least three, and n can be at least four or at least five or more. Typically, but not necessarily, n is at most ten.

Each target capture probe is capable of hybridizing to the support capture probe. The target capture probe typically includes a polynucleotide sequence U-1 that is complementary to a polynucleotide sequence U-2 in the support capture probe. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive).

As noted, the hybridizing the subset of n target capture probes to the support capture probe is performed at a hybridization temperature which is greater than a melting temperature $T_m$ of a complex between each individual target capture probe and the support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$. Hybridization of the target capture probes to the nucleic acids of interest and to the support capture probe can occur simultaneously or in either order.

At any of various steps, materials not captured on the solid support are optionally separated from the support. For example, after the target capture probes, nucleic acids, and support-bound support capture probe are hybridized, the solid support is optionally washed to remove unbound nucleic acids and target capture probes.

The methods can be used to capture the nucleic acids of interest from essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen.

Essentially all of the features noted for the embodiments above apply to these embodiments as well, as relevant.

An exemplary workflow illustrating capture of a specific DNA fragment, its conversion to double-stranded DNA, and preparation for sequencing on a Solexa instrument is schematically illustrated in FIG. 5. It will be evident that the specific techniques described are for the purposes of illustration only, and the techniques can be readily adapted to prepare a captured nucleic acid for sequencing by essentially any desired technique on essentially any instrumentation.

FIG. 5 Panel A schematically illustrates capture of an approximately 40 kb single-stranded DNA target (501) through cooperative hybridization of target capture probes 502 that hybridize near the two ends of target 501. Target capture probes 502 also hybridize to support capture probe 503, which is associated with solid support 504 (e.g., a well or bead). Blocking probes 505 hybridize to regions of target 501 adjacent to but not occupied by target capture probes

502. In this embodiment, capture occurs when all four target capture probes bind the same strand of the DNA target.

FIG. 5 Panel B schematically illustrates another configuration of the target capture probes for capture of an approximately 40 kb single-stranded DNA target (521) through cooperative hybridization of target capture probes 522. Target capture probes 522 are clustered within a small region of target 521. Target capture probes 522 also hybridize to support capture probe 523, which is associated with solid support 524 (e.g., a well or bead). Blocking probes 525 hybridize to regions of target 521 adjacent to but not occupied by target capture probes 522. The remaining steps are illustrated using the configuration of target capture probes shown in Panel B, but many other suitable configurations for the target capture probes will be evident.

In the example in FIG. 5, only the region of the target occupied by the probe set (target capture probes and optional blocking probes) is double-stranded (e.g., 400-600 bp of the 40 kb), while the remainder is single-stranded. However, for many next-generation sequencing protocols, short (e.g., 50-400 bp) double-stranded fragments need to be provided. As shown in FIG. 5 Panels C-D, random hexamer primers 530 are added and extended with a DNA polymerase to convert the single-stranded DNA to double-stranded. Optionally, blocking probes 525 flank both ends of the captured DNA, and thereby provide a primer that is completely complementary to the target DNA. The size of polymerized fragments 531 will vary depending, e.g., on the concentration of hexamer used, and there will be nicks in the newly polymerized strand between the 5' end of one polymerized fragment and the next 3' end. Optionally, the number of hexamers added is such that the average fragment size of the newly polymerized strand is about 1-2 kb.

The newly synthesized double-stranded DNA molecules are then converted to smaller fragments (e.g., 50-400 bp), e.g., by sonication (Elsner and Lindblad (1989) "Ultrasonic degradation of DNA" DNA 8:697-701), partial digestion with DNase I, or digestion with a restriction endonuclease (e.g., HaeIII). The treated sample is transferred to a fresh plate and treated, e.g., with Klenow fragment or T4 DNA polymerase, to create blunt ends (FIG. 5 Panel E). The blunt ended double-stranded DNAs are ligated to double-stranded adapters, e.g., asymmetric adapters (two different adapters, one of which is preferably ligated to one end of the fragment and the other to the other end), e.g., using T4 DNA ligase. The DNAs ligated with the asymmetric adapters are denatured and the single strands are injected into the Solexa flow cell. The single-stranded fragments bind randomly to the inside surface of the flow cell channel, which also includes a dense lawn of primers complementary to the adapters. Nucleotides and enzymes are added to initiate solid phase bridge amplification; see, e.g., Metzker (supra). Alternatively, specific regions of the 40 kb purified fragment can be amplified using PCR primers including adapters and prepared for sequencing.

As another example, instead of synthesizing a double-stranded DNA from the single-stranded DNA molecule captured on the support (e.g., target 521 in FIG. 5 Panel B), the single-stranded DNA molecule can be eluted from the support surface, e.g., by heating to 85° C., and transferred to a fresh well. The eluted single-stranded DNA target is then partially digested with S1 and/or Mung Bean nuclease or fragmented by sonication to create smaller molecules. (The target capture probes and optional blocking probes are typically also partially digested during this process.) Single-stranded adapters are ligated to these smaller (e.g., 50-400 nucleotides) single-stranded DNA molecules using T4 RNA ligase. The adaptors are in huge excess over the remaining capture extenders and blocking probes. T4 RNA ligation of single-stranded DNAs is not as efficient as T4 DNA ligation of double-stranded DNAs; thus a PCR amplification is optionally performed; see Zhang and Chiang (1996) "Single-stranded DNA ligation by T4 RNA ligase for PCR cloning of 5'-noncoding fragments and coding sequence of a specific gene" Nuc. Acids Res 24:990-991, Edwards et al. (1991) Nucleic Acids Res. 19:5227-5232, and Tessier et al. (1986) Anal. Biochem. 158:171-178. The short single-stranded DNA fragments bearing the adapters are then denatured to remove any secondary structure and injected into the Solexa flow cell as described above.

As another example, for real-time single molecule sequencing in a zero mode waveguide, e.g., the SMRT sequencing system from Pacific Biosciences, a single-stranded DNA can be captured and converted to double-stranded form using random hexamer primers as described above. A lower concentration of hexamers can be employed if longer templates are desired, since the SMRT system does not require very short templates. The double-stranded DNA is fragmented if necessary, e.g., by restriction enzyme digestion, and hairpin adapters are then ligated to the ends of the fragments; see, e.g., Travers et al. (2010) "A flexible and efficient template format for circular consensus sequencing and SNP detection" Nucl Acids Res 38:e159 and Eid et al. (2009) "Real-time DNA sequencing from single polymerase molecules" Science 323:133-138. Alternatively, the captured single-stranded DNA can be eluted, converted to double-stranded form, fragmented if necessary, and ligated to the hairpin adapters.

Figure 6A:
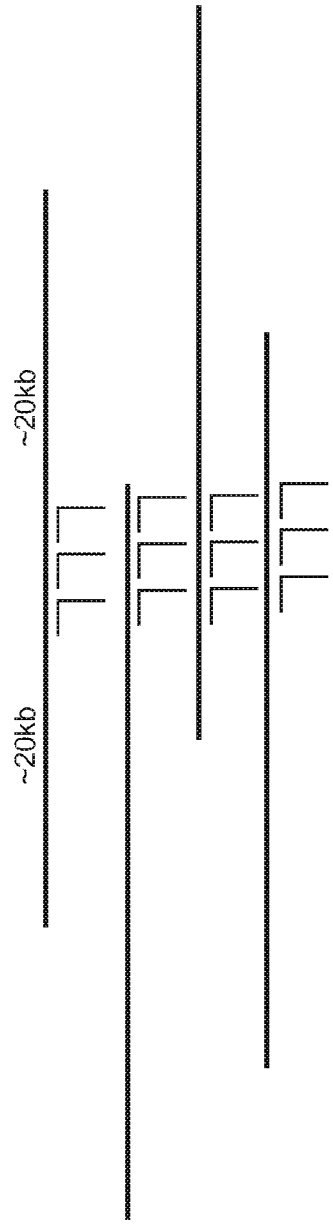
FIG. 6 Panels A and B illustrate capture of two sets of nucleic acid fragments providing overlapping sequence data.
Figure 6B:
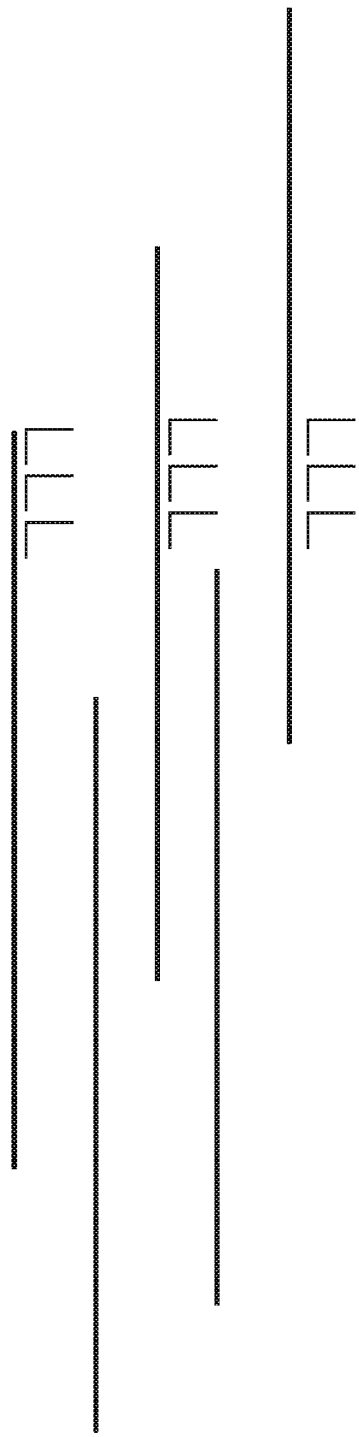

Capture of nucleic acid targets through cooperative hybridization for sequencing offers a number of advantages. For example, no nucleic acid purification is required: although nucleic acids can be captured from samples of purified or extracted nucleic acids, they can also be captured from crude cell or tissue lysates (see, e.g., U.S. patent publication 2007/0161015 "Detection of nucleic acids from whole blood"). Desired nucleic acid targets (e.g., DNAs and/or RNAs) can be captured with high specificity. Capture is not biased as for some other techniques, thus even GC-rich or repetitive regions can be recovered. The techniques provide ample quantities of nucleic acid: Solexa, for example, typically requires a minimum of 30-60 pg of target per run, while the methods can readily capture 600 ng of DNA (for humans, equivalent to 200,000 cell equivalents or 200,000 genomes or 200,000 specific gene regions captured by hybridization) per well. A large quantity of samples can be processed, e.g., in multiwell plate format (e.g., 96 or 384 well plates) due to the ease of workflow. Use of magnetic beads permits low cost processing, provides fast turnaround time, and provides the ability to easily mix and match plex level (particularly as compared to arrays such as NimbleGen). Multiple targets can be captured, e.g., per well or in adjacent wells, and these targets can be continuous or non-continuous (e.g., on different chromosomes). For example, where sequence information from a large portion of a chromosome is desired, adjacent sets of overlapping fragments can be captured. As schematically illustrated in FIG. 6 Panel A, a set of overlapping DNA fragments each containing a region complementary to a set of target capture probes is captured in one well (e.g., a 40 kb genomic fragment is captured with target capture probes hybridizing within a 400-600 by region). In a second well, a different target capture probe set shifted by about 20 kb downstream is employed, as shown in FIG. 6 Panel B. Two of the fragments captured by the target capture probe set of Panel A are not captured by the target capture probe set of Panel B, but an additional fragment that extends further downstream is captured by the target capture probes of Panel B (though not by those of Panel A). Similarly, capture of long nucleic acids aids assembly of short stretches of sequence derived from the nucleic acids.

Compositions

Compositions related to the methods are another feature of the invention. Thus, one general class of embodiments provides a composition that includes two or more subsets of particles and two or more subsets of n target capture probes, wherein n is at least two. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. When the nucleic acid of interest corresponding to a subset of n target capture probes is present in the composition and is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe.

In one preferred class of embodiments, a plurality of the particles in each subset are distinguishable from a plurality of the particles in every other subset. Typically, substantially all of the particles in each subset are distinguishable from substantially all of the particles in every other subset. Alternatively, the particles comprising the various subsets are not distinguishable.

The composition optionally includes a sample comprising or suspected of comprising at least one of the nucleic acids of interest, e.g., two or more, three or more, etc. nucleic acids. In one class of embodiments, the composition comprises one or more of the nucleic acids of interest. Each nucleic acid of interest is hybridized to its corresponding subset of n target capture probes, and the corresponding subset of n target capture probes is hybridized to its corresponding support capture probe. Each nucleic acid of interest is thus associated with a subset of the particles. The composition is maintained at the hybridization temperature.

As noted, the hybridization temperature is greater than the $T_m$ of each of the individual target capture probe-support capture probe complexes. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the methods above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

As noted, even nucleic acids present at low concentration can be captured. Thus, in one class of embodiments, at least one of the nucleic acids of interest is present in the composition in a non-zero amount of 200 amol or less, 150 amol or less, 100 amol or less, 50 amol or less, 10 amol or less, 1 amol or less, or even 0.1 amol or less, 0.01 amol or less, 0.001 amol or less, or 0.0001 amol or less. Similarly, two nucleic acids of interest can be captured simultaneously, even when they differ in concentration by 1000-fold or more in the composition.

Capture of a particular nucleic acid on the particles is optionally quantitative. Thus, in one exemplary class of embodiments, the composition includes a first nucleic acid of interest, and at least 30%, at least 50%, at least 80%, at least 90%, at least 95%, or even at least 99% of a total amount of the first nucleic acid present in the composition is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the composition comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the composition, is captured on a first subset of particles, while the second nucleic acid comprises 1% or less of a total amount of nucleic acid captured on the first subset of particles (e.g., 0.5% or less, 0.2% or less, or even 0.1% or less). The second nucleic acid can be another nucleic acid of interest or simply any nucleic acid. Typically, target capture probes are chosen that hybridize to regions of the first nucleic acid having the greatest sequence difference from the second nucleic acid.

In one exemplary class of embodiments in which related nucleic acids are differentially captured, the composition comprises a first nucleic acid of interest and a second nucleic acid, where the first nucleic acid is a first splice variant and the second nucleic acid is a second splice variant of a given mRNA. A first subset of n target capture probes is capable of hybridizing to the first splice variant, of which at most n−1 target capture probes are capable of hybridizing to the second splice variant. Optionally, at least 80% or more, 90% or more, or 95% or more of the first splice variant is captured on a first subset of particles while at most 10% or less, 5% or less, 3% or less, or 1% or less of the second splice variant is captured on the first subset of particles. Preferably, a first subset of n target capture probes is hybridized to the first splice variant, whereby the first splice variant is captured on a first subset of particles, and at most n−1 of the target capture probes are hybridized to the second splice variant, whereby the second splice variant is not captured on the first subset of particles.

In one class of embodiments, the composition includes one or more of the nucleic acids of interest, each of which includes a label or is configured to bind to a label. The composition optionally includes one or more of: a cell lysate, an intercellular fluid, a bodily fluid, a conditioned culture medium, a polynucleotide complementary to a nucleic acid of interest and comprising a label, or a reagent used to amplify nucleic acids (e.g., a DNA polymerase, an oligonucleotide primer, or nucleoside triphosphates).

A related general class of embodiments provides a composition comprising two or more subsets of particles, two or more subsets of n target capture probes, wherein n is at least two, and at least a first nucleic acid of interest. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. In this class of embodiments, the composition is maintained at a hybridization temperature, which hybridization temperature is greater than a melting temperature $T_m$ of a complex between each individual target capture probe and its corresponding support capture probe. The first nucleic acid of interest is hybridized to a first subset of n first target capture probes, which first target capture probes are hybridized to a first support capture probe.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, use of labeled nucleic acids of interest, label configuration, type of particles, additional components of the composition, source of the sample and/or nucleic acids, and/or the like. Preferably, a plurality of the particles in each subset are distinguishable from a plurality of the particles in every other subset. (Typically, substantially all of the particles in each subset are distinguishable from substantially all of the particles in every other subset.)

Another general class of embodiments provides a composition that includes a solid support comprising two or more support capture probes, each of which is provided at a selected position on the solid support, and two or more subsets of n target capture probes, wherein n is at least two. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support.

The composition optionally includes a sample comprising or suspected of comprising at least one of the nucleic acids of interest, e.g., two or more, three or more, etc. nucleic acids. In one class of embodiments, the composition includes at least a first nucleic acid of interest and is maintained at a hybridization temperature. The first nucleic acid of interest is hybridized to a first subset of n first target capture probes, which first target capture probes are hybridized to a first support capture probe; the first nucleic acid is thereby associated with a first selected position on the solid support. It will be evident that the composition optionally includes second, third, etc. nucleic acids of interest, which are likewise associated with second, third, etc. selected positions on the solid support through association with second, third, etc. subsets of target capture probes and second, third, etc. support capture probes. The hybridization temperature is greater than a melting temperature $T_m$ of a complex between each individual target capture probe and its corresponding support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the embodiments above apply to these embodiments as well, as relevant; for example, with respect to number of target capture probes per subset, type of solid support, configuration of the target capture probes and/or support capture probes, number of nucleic acids of interest and of selected positions on the solid support and subsets of target capture probes, use of labeled nucleic acids of interest, label configuration, additional components of the composition, source of the sample and/or nucleic acids, and/or the like.

Another general class of embodiments provides a composition that includes a solid support having associated therewith a support capture probe. The composition also includes two or more subsets of n target capture probes (typically, n different target capture probes), wherein n is at least two. A different subset of target capture probes is provided for each different nucleic acid of interest, and the target capture probes in each subset are capable of hybridizing to nonoverlapping polynucleotide sequences in the corresponding nucleic acid of interest. The target capture probes in each subset are also capable of hybridizing to the support capture probe.

The composition optionally includes the two or more different nucleic acids of interest. Optionally, the composition is maintained at a hybridization temperature, which hybridization temperature is greater than a melting temperature $T_m$ of a complex between each individual target capture probe and the support capture probe, and the nucleic acids of interest are hybridized to the target capture probes, which target capture probes are hybridized to the support capture probe.

Essentially all of the features noted for the embodiments above apply to these embodiments as well, as relevant; for example, with respect to number of target capture probes per subset, configuration of the target capture probes and/or support capture probe(s), number of nucleic acids of interest and of subsets of target capture probes, type of solid support (e.g., different subsets of distinguishable particles bearing different support capture probes, a single type of particle bearing a single support capture probe, a multiwell plate, or a spatially addressable solid support), label configuration, source of the sample and/or nucleic acids, and/or the like. The composition is optionally used to purify the nucleic acids of interest for further manipulation, e.g., prior to sequencing.

Yet another general class of embodiments provides a composition that includes one or more nucleic acid of interest, which nucleic acid is at least 20 kilobases in length, a solid support having associated therewith a support capture probe, and one or more subset of n target capture probes (e.g., n different target capture probes), wherein n is at least two. The target capture probes in each subset are capable of hybridizing to nonoverlapping polynucleotide sequences in the corresponding nucleic acid of interest, and are also capable of hybridizing to the support capture probe.

Essentially all of the features noted for the embodiments above apply to these embodiments as well, as relevant; for example, with respect to number of target capture probes per subset, configuration of the target capture probes and/or support capture probe(s), number of nucleic acids of interest and of subsets of target capture probes, type of solid support, label configuration, type and length of nucleic acids of interest, source of the sample and/or nucleic acids, and/or the like.

Kits

Yet another general class of embodiments provides a kit for capturing two or more nucleic acids of interest. The kit includes two or more subsets of particles and two or more subsets of n target capture probes, wherein n is at least two, packaged in one or more containers. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. When the nucleic acid of interest corresponding to a subset of n target capture probes is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe. The kit optionally also includes instructions for using the kit to capture and optionally detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, source of the sample and/or nucleic acids, type of particles, label configuration, and/or the like. Preferably, a plurality of the particles in each subset are distinguishable from a plurality of the particles in every other subset. (Typically, substantially all of the particles in each subset are distinguishable from substantially all of the particles in every other subset.)

A related general class of embodiments provides a kit for capturing two or more nucleic acids of interest. The kit includes a solid support comprising two or more support capture probes, each of which is provided at a selected position on the solid support, and two or more subsets of n target capture probes, wherein n is at least two, packaged in one or more containers. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support.

In one class of embodiments, when a nucleic acid of interest corresponding to a subset of n target capture probes is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

The kit optionally also includes instructions for using the kit to capture and optionally detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of target capture probes per subset, configuration of the target capture probes and/or support capture probes, number of nucleic acids of interest and of selected positions on the solid support and subsets of target capture probes, type of support, label configuration, source of the sample and/or nucleic acids, and/or the like.

Another general class of embodiments provides a kit for capturing one or more nucleic acid. The kit includes a solid support and one or more subset of n different target capture probes, wherein n is at least two. The solid support has associated therewith a support capture probe. The target capture probes in each subset are capable of hybridizing to nonoverlapping polynucleotide sequences in the corresponding nucleic acid of interest and are also capable of hybridizing to the support capture probe. Instructions for capturing the one or more nucleic acid of interest with the solid support and the target capture probes are also included, optionally along with instructions for isolating the nucleic acids, removal of the target capture probes from the nucleic acids, removal of the nucleic acids from the support, and/or further manipulation of the nucleic acids. The elements of the kit are generally packaged in one or more containers.

In one class of embodiments, the kit includes two or more subsets of n different target capture probes for capture of two or more different nucleic acids; a different subset of target capture probes is provided for each different nucleic acid of interest. The kit optionally also includes one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, type of solid support (e.g., different subsets of distinguishable particles bearing different support capture probes, a single type of particle bearing a single support capture probe, a multiwell plate, or a spatially addressable solid support), source of the sample and/or nucleic acids, and/or the like.

Yet another general class of embodiments provides a kit for capturing and preparing one or more nucleic acid of interest for sequencing. The kit includes a solid support having associated therewith a support capture probe, one or more subset of n different target capture probes, wherein n is at least two, one or more oligonucleotide adaptors (single or double stranded), a nucleic acid ligase, and instructions for isolating the one or more nucleic acid of interest with the solid support and the target capture probes and for preparing the isolated one or more nucleic acid for sequencing with the one or more adaptors and the ligase. The target capture probes in each subset are capable of hybridizing to nonoverlapping polynucleotide sequences in the corresponding nucleic acid of interest and are also capable of hybridizing to the support capture probe. The elements of the kit are generally packaged in one or more containers.

In one class of embodiments, the kit includes two or more subsets of n different target capture probes for capture of two or more different nucleic acids; a different subset of target capture probes is provided for each different nucleic acid of interest. The kit optionally also includes one or more buffered solutions (e.g., lysis buffer, diluent, hybridization buffer, ligation buffer, and/or wash buffer), one or more additional enzymes (e.g., a nuclease, restriction enzyme and/or polymerase), and/or the like.

Essentially all of the features noted for the embodiments above apply to these embodiments as well, as relevant; for example, with respect to number of target capture probes per subset, configuration of the target capture probes and/or support capture probes, number of nucleic acids of interest and of subsets of target capture probes, type of solid support (e.g., different subsets of distinguishable particles bearing different support capture probes, a single type of particle bearing a single support capture probe, a multiwell plate, or a spatially addressable solid support), source of the sample and/or nucleic acids, and/or the like.

Systems

In one aspect, the invention includes systems, e.g., systems used to practice the methods herein and/or comprising the compositions described herein. The system can include, e.g., a fluid and/or particle (e.g., microsphere) handling element, a fluid and/or particle containing element, a laser for exciting a fluorescent label and/or fluorescent microspheres, a detector for detecting light emissions from a chemiluminescent reaction or fluorescent emissions from a fluorescent label and/or fluorescent microspheres, a thermal cycler, and/or a robotic element that moves other components of the system from place to place as needed (e.g., a multiwell plate handling element). For example, in one class of embodiments, a composition of the invention is contained in a flow cytometer, a Luminex 100™ or HTS™ a microplate reader, a microarray reader, a luminometer, a colorimeter, an automated nucleic acid sequencer, or like instrument. In one class of embodiments, the system automates capture, isolation, detection, amplification, manipulation, and/or polynucleotide sequence determination of one or more of the nucleic acids of interest.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Labels

A wide variety of labels are well known in the art and can be adapted to the practice of the present invention. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., Haughland (2003) Handbook of Fluorescent Probes and Research Products, Ninth Edition or Web Edition, from Molecular Probes, Inc., or The Handbook: A Guide to Fluorescent Probes and Labeling Technologies, Tenth Edition or Web Edition (2006) from Invitrogen (available on the world wide web at probes.invitrogen.com/handbook) for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polynucleotides, during synthesis or by postsynthetic reactions by techniques established in the art; for example, kits for fluorescently labeling polynucleotides with various fluorophores are available from Molecular Probes, Inc. ((www.) molecularprobes.com), and fluorophore-containing phosphoramidites for use in nucleic acid synthesis are commercially available, as are fluorophore-containing nucleotides (e.g., Cy3 or Cy5 labeled dCTP, dUTP, dTTP, and the like). Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Particles

Microspheres are preferred particles in certain embodiments described herein since they are generally stable, are widely available in a range of materials, surface chemistries and uniform sizes, and can be fluorescently dyed. Microspheres can optionally be distinguished from each other by identifying characteristics such as their size (diameter) and/or their fluorescent emission spectra, for example.

Luminex Corporation ((www.) luminexcorp.com), for example, offers 100 sets of uniform diameter polystyrene microspheres. The microspheres of each set are internally labeled with a distinct ratio of two fluorophores. A flow cytometer, particle sorter, or other suitable instrument can thus be used to classify each individual microsphere according to its predefined fluorescent emission ratio (and optionally to isolate one or more desired sets of microspheres along with any captured nucleic acid). Fluorescently-coded microsphere sets are also available from a number of other suppliers, including Radix Biosolutions ((www.) radixbiosolutions.com) and Upstate Biotechnology ((www.) upstatebiotech.com). Alternatively, BD Biosciences ((www.) bd.com) and Bangs Laboratories, Inc. ((www.) bangslabs.com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]:25). For example, microspheres with carboxyl, hydrazide or maleimide groups are available and permit covalent coupling of molecules (e.g., polynucleotide support capture probes with free amine, carboxyl, aldehyde, sulfhydryl or other reactive groups) to the microspheres. As another example, microspheres with surface avidin or streptavidin are available and can bind biotinylated support capture probes; similarly, microspheres coated with biotin are available for binding support capture probes conjugated to avidin or streptavidin. In addition, services that couple a capture reagent of the customer's choice to microspheres are commercially available, e.g., from Radix Biosolutions ((www.) radixbiosolutions.com).

Protocols for using such commercially available microspheres (e.g., methods of covalently coupling polynucleotides to carboxylated microspheres for use as support capture probes, methods of blocking reactive sites on the microsphere surface that are not occupied by the polynucleotides, methods of binding biotinylated polynucleotides to avidin-functionalized microspheres, and the like) are typically supplied with the microspheres and are readily utilized and/or adapted by one of skill. In addition, coupling of reagents to microspheres is well described in the literature.

For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the FlowMetrix™ system" Clinical Chemistry 44:2057-2060; Gordon and McDade (1997) "Multiplexed quantification of human IgG, IgA, and IgM with the FlowMetrix™ system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled nucleic acid) on each subset are commercially available. For example, flow cytometers are widely available, e.g., from Becton-Dickinson ((www.) bd.com) and Beckman Coulter ((www.) beckman.com). Luminex 100™ and Luminex HTS™ (which use microfluidics to align the microspheres and two lasers to excite the microspheres and the label) are available from Luminex Corporation ((www.) luminexcorp.com); the similar BioPlex™ Protein Array System is available from Bio-Rad Laboratories, Inc. ((www.) bio-rad.com). A confocal microplate reader suitable for microsphere analysis, the FMAT™ System 8100, is available from Applied Biosystems ((www.) appliedbiosystems.com).

As another example of particles that can be adapted for use in the present invention, sets of microbeads that include optical barcodes are available from CyVera Corporation ((www.) cyvera.com). The optical barcodes are holographically inscribed digital codes that diffract a laser beam incident on the particles, producing an optical signature unique for each set of microbeads.

Non-spherical particles can also be employed in the methods, compositions, kits, and systems described herein. Accordingly, as yet another example of particles that can be adapted for use in the present invention, next generation microparticles have been disclosed recently where the particle comprises a barcode that is detectable by visible light. For instance, see U.S. Pat. Nos. 7,745,091 and 7,745,092 and U.S. patent application Ser. Nos. 11/521,115, 11/521, 058, 11/521,153, and 12/215,607 and related applications, all of which are incorporated herein by reference in their entirety for all purposes. This microparticle technology allows detection of hundreds of nucleic acid targets in a single sample or assay with ease, using the unique barcode contained in each particle, assignable to a specific nucleic acid of interest through assignment of the support capture probe associated with that particle.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., Current Protocols, a joint venture between Greene Publishing Associates, Inc. and John Wiley & Sons, Inc., (supplemented through 2010). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references.

In addition, essentially any polynucleotide (including, e.g., labeled or biotinylated polynucleotides) can be custom or standard ordered from any of a variety of commercial sources, such as The Midland Certified Reagent Company ((www.) mcrc.com), The Great American Gene Company ((www.) genco.com), ExpressGen Inc. ((www.) expressgen.com), Qiagen (oligos.qiagen.com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology ((www.) piercenet.com). Similarly, any nucleic acid can be fluorescently labeled, for example, by using commercially available kits such as those from Molecular Probes, Inc. ((www.) molecularprobes.com) or Pierce Biotechnology ((www.) piercenet.com), by incorporating a fluorescently labeled phosphoramidite during chemical synthesis of a polynucleotide, or by incorporating a fluorescently labeled nucleotide during enzymatic synthesis of a polynucleotide.

Arrays

In an array of support capture probes on a solid support (e.g., a membrane, a glass or plastic slide, a silicon or quartz chip, a plate, or other spatially addressable solid support), each support capture probe is typically bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent SurePrint Technology: Content centered microarray design enabling speed and flexibility" available on the web at chem.agilent.com/temp/rad01539/00039489.pdf; and references therein. Arrays of pre-synthesized polynucleotides can be formed (e.g., printed), for example, using commercially available instruments such as a GMS 417 Arrayer (Affymetrix, Santa Clara, Calif.). Alternatively, the polynucleotides can be synthesized at the selected positions on the solid support; see, e.g., U.S. Pat. Nos. 6,852,490 and 6,306,643, each to Gentanlen and Chee entitled "Methods of using an array of pooled probes in genetic analysis."

Suitable solid supports are commercially readily available. For example, a variety of membranes (e.g., nylon, PVDF, and nitrocellulose membranes) are commercially available, e.g., from Sigma-Aldrich, Inc. ((www.) sigmaaldrich.com). As another example, surface-modified and pre-coated slides with a variety of surface chemistries are commercially available, e.g., from TeleChem International ((www.) arrayit.com), Corning, Inc. (Corning, N.Y.), or Greiner Bio-One, Inc. ((www.) greinerbiooneinc.com). For example, silanated and silyated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated support capture probes. In addition, services that produce arrays of polynucleotides of the customer's choice are commercially available, e.g., from TeleChem International ((www.) arrayit.com) and Agilent Technologies (Palo Alto, Calif.).

Suitable instruments, software, and the like for analyzing arrays to distinguish selected positions on the solid support and to detect the presence or absence of a label (e.g., a fluorescently labeled nucleic acid) at each position are commercially available. For example, microarray readers are available, e.g., from Agilent Technologies (Palo Alto, Calif.), Affymetrix (Santa Clara, Calif.), and Zeptosens (Switzerland).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Multiplex Capture of Nucleic Acids

The following sets forth a series of experiments that demonstrate design of support capture probes and corresponding target capture probes for multiplex capture of nucleic acids. Unique sequences of 15 bases were chosen as support capture probes. The support capture probes were designed to have minimal potential for secondary structure formation or cross-hybridization. They were also screened against homology with sequences of human, mouse or rat genes. Oligonucleotide support capture probes were synthesized with 5'-amino linker (BioSearch) and covalently linked to carboxylated fluorescent-encoded microsphere beads (Luminex Corporation) following the recommended conjugation procedure from Luminex Each support capture probe was coupled to a different, fluorescently-labeled subset of the beads.

Figure 4:
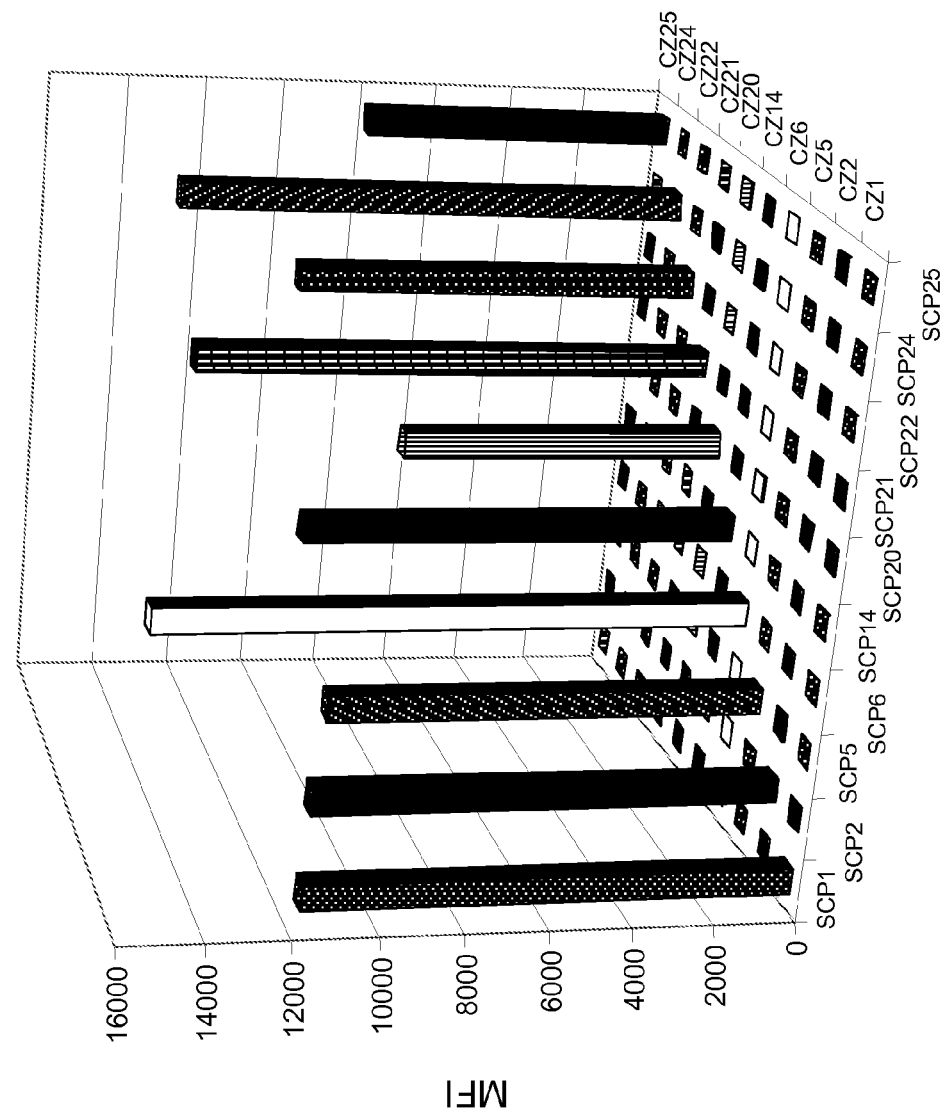
FIG. 4 depicts a graph illustrating evaluation of ten support capture probes for cross hybridization with ten biotin-labeled probes, one complementary to each of the support capture probes. Biotin-labeled probes are named on the x-axis, beads with associated support capture probes are represented by number on the y-axis, and median fluorescent intensity is plotted on the z-axis.
Figure 5A:
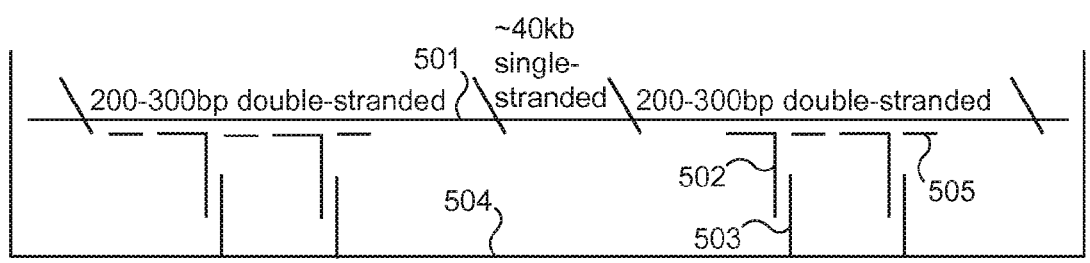
FIG. 5 Panels A-E schematically illustrate capture of a DNA fragment and its preparation for use in sequence determination.
Figure 5B:
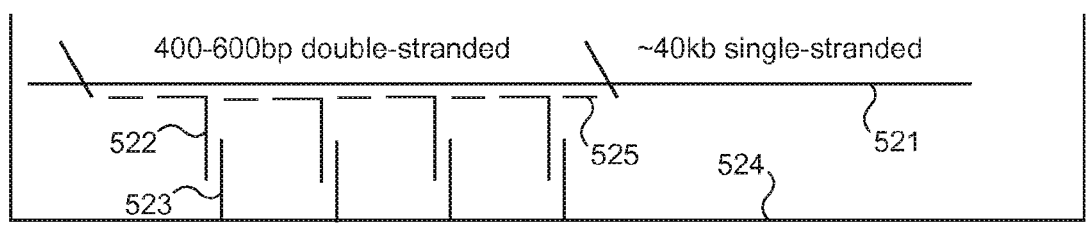
Figure 5C:
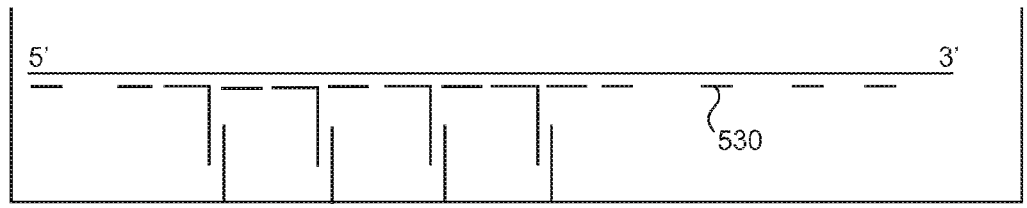
Figure 5D:
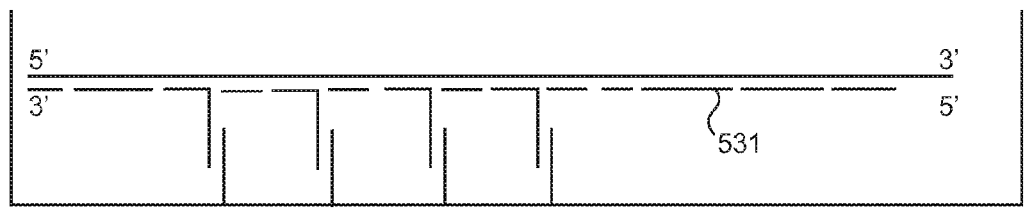
Figure 5E:
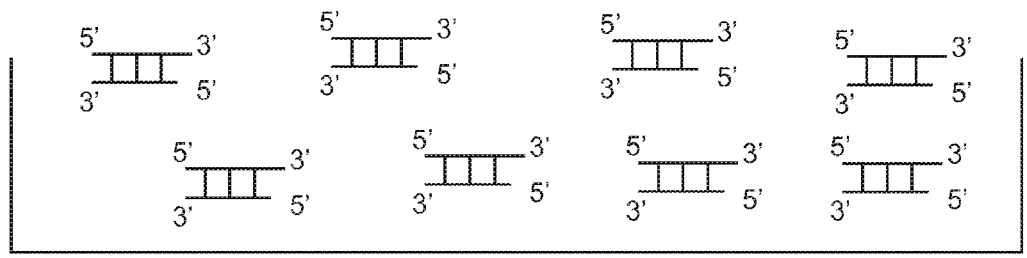

Each bead subset was examined for specific hybridization to a biotinylated oligonucleotide complementary to the support capture probe associated with that subset of beads, as well as for its non-specific hybridization to the other biotinylated oligonucleotides. The biotinylated oligonucleotides were detected with streptavidin-conjugated R-phycoerythrin. As illustrated in FIG. 4, when 16.5 fmol of an individual biotin-labeled complementary probe (represented by name in x-axis) is added into a mixture of ten support capture probe-conjugated beads, only the corresponding bead (represented by the SCP number in y-axis) gives strong fluorescent signal (z-axis, background subtracted median fluorescent intensity from 100 counted beads); the other beads show minimal fluorescent signal above background. The assay signals of all possible non-specific hybridizations were less than 0.1% of those observed for the perfectly matched pair, indicating a very high degree of hybridization specificity. Thus the set of support capture probes was shown to be highly specific and can be used for multiplex capture of target nucleic acids.

Ten subsets of target capture probes were designed. Each target capture probe is complementary to one of the ten support capture probes and to one of ten target nucleic acids. The subsets of target capture probes can be used in conjunction with the support capture probe-conjugated beads (or, e.g., with a support capture probe-conjugated spatially addressable solid support) to specifically capture, e.g., mRNAs or the like produced from the genes listed in Table 1. Sequences of the support capture probes and target capture probes are presented in Table 2.

For example, one or more of the target nucleic acids is optionally captured by hybridization to the corresponding subset of target capture probes, which is in turn hybridized to the corresponding support-bound support capture probe, under any of a variety of suitable hybridization conditions. As one example, the target nucleic acids are optionally captured by hybridization in a solution that includes 127 mM LiCl, 5% lithium lauroyl sulfate, 9 mM EDTA, 50 mM HEPES (pH 7.5), 0.05% hespan (DuPont Pharmaceuticals), 0.05% ProClin 300 (Supelco), and 0.2% casein (Research Organics, Hammarsten quality), along with the target nucleic acid(s), support-bound support capture probes, and target capture probes (e.g., about 16.5 fmol of each target capture probe in a 100 µl assay volume), at a hybridization temperature of 53° C. for about 16 hours. The support is optionally washed, e.g., with a wash buffer that includes 0.1×SSC and 0.3% lithium lauryl sulfate, to remove materials not captured on the support.

About 2000 beads per subset are typically used for capture and optional detection of the listed mRNAs, e.g., from cell lysates. It will be evident, however, that the number of particles (e.g., beads) per subset is optionally optimized for the desired application. For example, the number of particles per subset can be increased, e.g., in embodiments in which capture of substantially all of a particular nucleic acid of interest present in a sample is desired (including, e.g., embodiments in which the nucleic acid is present at very low concentration), or decreased, e.g., to increase sensitivity of detection for a nucleic acid of interest present at very low concentration in the sample by maximizing the number of molecules of that nucleic acid captured per bead in embodiments in which fluorescently labeled nucleic acids are being detected. By increasing the number of particles used, even less than 0.001 amol or 10-50 copies of a target nucleic acid can optionally be captured (and subsequently amplified, detected, or the like, if desired).

TABLE 1

Target names and reference sequence accession numbers for the target nucleic acids.

| Target Symbol | Accession Number |
|---|---|
| IL2 | NM_000586 |
| TNF | NM_000594 |
| VEGF | NM_003376 |
| IL10 | NM_000572 |
| IL6 | NM_000600 |
| IL1B | NM_000576 |
| IFNG | NM_000619 |
| IL8 | NM_000584 |
| CSF2 | NM_000758 |
| GAPD | NM_002046 |

TABLE 2

Support capture probe (SCP) and target capture probe (TCP) sequences for multiplex capture of the targets listed in Table 1.

| Gene Name | | | SEQ ID NO |
|---|---|---|---|
| CSF2 | TCP | agcagcaggctctgcagcTTTTTttgtgcagtgttata | 1 |
| CSF2 | TCP | gcgggtgcagagatgctgTTTTTttgtgcagtgttata | 2 |
| CSF2 | TCP | tacagctccaggcgggtcTTTTTttgtgcagtgttata | 3 |
| CSF2 | TCP | tgagcttggtgaggctgccTTTTTttgtgcagtgttata | 4 |
| CSF2 | TCP | tgcttgtagtggctggccaTTTTTttgtgcagtgttata | 5 |
| CSF2 | SCP (CP24) | TTTTTTTTTATAACACTGCACAA | 6 |
| GAPD | TCP | tgacggtgccatggaatttTTTTTaaaactatacgtgct | 7 |
| GAPD | TCP | agcttcccgttctcagcctTTTTTaaaactatacgtgct | 8 |
| GAPD | TCP | tctcgctcctggaagatggtTTTTTaaaactatacgtgct | 9 |
| GAPD | TCP | gcaaatgagccccagccTTTTTaaaactatacgtgct | 10 |
| GAPD | TCP | cctttggctccccccctTTTTTaaaactatacgtgct | 11 |
| GAPD | TCP | catggatgaccttggccagTTTTTaaaactatacgtgct | 12 |
| GAPD | TCP | gctcagggatgaccttgccTTTTTaaaactatacgtgct | 13 |
| GAPD | SCP (CP25) | TTTTTTTTAGCACGTATAGTTTT | 14 |
| IFNG | TCP | cactctcctctttccaattcttcaTTTTTTTttcacacacattaac | 15 |
| IFNG | TCP | ttggctctgcattattttctgtTTTTTttcacacacattaac | 16 |
| IFNG | TCP | tctcgtttcttttgttgctattgTTTTTttcacacacattaac | 17 |
| IFNG | TCP | atgagttcatgtattgctttgcgtTTTTTttcacacacattaac | 18 |
| IFNG | TCP | ttccctgttttagctgctggTTTTTttcacacacattaac | 19 |
| IFNG | TCP | atattccccatataaataatgttaaatattTTTTTttcacacacattaac | 20 |
| IFNG | SCP (CP20) | TTTTTTTTGTTAATGTGTGTGAA | 21 |

TABLE 2-continued

Support capture probe (SCP) and target capture probe (TCP)
sequences for multiplex capture of the targets listed in Table 1.

| Gene Name | | | SEQ ID NO |
|---|---|---|---|
| IL1 | TCP | agtgggtgcagctgttctcaTTTTTccgtgcttttctaat | 22 |
| IL1 | TCP | ctcggagatctcgaagcatgtTTTTTccgtgcttttctaat | 23 |
| IL1 | TCP | gctgatccttcatttgaaagaaaTTTTTccgtgcttttctaat | 24 |
| IL1 | TCP | ctgggtcttggttctcagcttTTTTTccgtgcttttctaat | 25 |
| IL1 | TCP | gcctcagcctgagggtcttTTTTTccgtgcttttctaat | 26 |
| IL1 | TCP | ccgattttggagacctctaatttaTTTTTccgtgcttttctaat | 27 |
| IL1 | SCP (CP5) | TTTTTTTTATTAGAAAAGCACGG | 28 |
| IL1B | TCP | gcagaggtccaggtcctggTTTTTaacgtgtattccatt | 29 |
| IL1B | TCP | tgaagcccttgctgtagtggtTTTTTaacgtgtattccatt | 30 |
| IL1B | TCP | cctggaaggtctgtgggcaTTTTTaacgtgtattccatt | 31 |
| IL1B | TCP | aaagaaggtgctcaggtcattctTTTTTaacgtgtattccatt | 32 |
| IL1B | TCP | ggagagctttcagttcatatggaTTTTTaacgtgtattccatt | 33 |
| IL1B | TCP | ccatatcctgtccctggaggtTTTTTaacgtgtattccatt | 34 |
| IL1B | TCP | attcttttccttgaggcccaTTTTTaacgtgtattccatt | 35 |
| IL1B | SCP (CP14) | TTTTTTTTAATGGAATACACGTT | 36 |
| IL2 | TCP | tgagtttgggattcttgtaattattaaTTTTTgaagttaccgttttc | 37 |
| IL2 | TCP | tggccttcttgggcatgtaTTTTTgaagttaccgttttc | 38 |
| IL2 | TCP | ctccagaggtttgagttcttcttcTTTTTgaagttaccgttttc | 39 |
| IL2 | TCP | tcagatcccctttagttccagaactTTTTTgaagttaccgttttc | 40 |
| IL2 | TCP | aataaatagaaggcctgatatgttttaTTTTTgaagttaccgttttc | 41 |
| IL2 | SCP (CP1) | TTTTTTTTGAAAACGGTAACTTC | 42 |
| IL6 | TCP | gagcttctctttcgttcccgTTTTTggggaacatagaaaa | 43 |
| IL6 | TCP | tgtggagaaggagttcatagctgTTTTTggggaacatagaaaa | 44 |
| IL6 | TCP | agccccagggagaaggcTTTTTggggaacatagaaaa | 45 |
| IL6 | TCP | tgtctcctttctcagggctgaTTTTTggggaacatagaaaa | 46 |
| IL6 | TCP | cctcattgaatccagattggaaTTTTTggggaacatagaaaa | 47 |
| IL6 | TCP | gaagagccctcaggctggaTTTTTggggaacatagaaaa | 48 |
| IL6 | SCP (CP6) | TTTTTTTTTTTCTATGTTCCCC | 49 |
| IL8 | TCP | tgcacccagttttccttggTTTTTttcaaatgttagcct | 50 |
| IL8 | TCP | ttttatgaattctcagccctcttTTTTTttcaaatgttagcct | 51 |
| IL8 | TCP | cggatattctcttggcccttTTTTTttcaaatgttagcct | 52 |
| IL8 | TCP | tgtggatcctggctagcagaTTTTTttcaaatgttagcct | 53 |
| IL8 | TCP | acccaattgtttgtttgtttaatcTTTTTttcaaatgttagcct | 54 |
| IL8 | SCP (CP22) | TTTTTTTTAGGCTAACATTTGAA | 55 |

TABLE 2 -continued

Support capture probe (SCP) and target capture probe (TCP) sequences for multiplex capture of the targets listed in Table 1.

| Gene Name | | | SEQ ID NO |
|---|---|---|---|
| TNF | TCP | cgagaagatgatctgactgcctgTTTTTctgagtcaaagcatt | 56 |
| TNF | TCP | gctgccctcagcttgagTTTTTctgagtcaaagcatt | 57 |
| TNF | TCP | gtctggtaggagacggcgatTTTTTctgagtcaaagcatt | 58 |
| TNF | TCP | tcccagatagatgggctcatacTTTTTctgagtcaaagcatt | 59 |
| TNF | TCP | tcgggccgattgatctcaTTTTTctgagtcaaagcatt | 60 |
| TNF | TCP | cccccaattctcttttgagcTTTTTctgagtcaaagcatt | 61 |
| TNF | SCP (CP2) | TTTTTTTTAATGCTTTGACTCAG | 62 |
| VEGF | TCP | aaggctccaatgcacccaTTTTTaggttttggattcat | 63 |
| VEGF | TCP | ctgccatgggtgcagccTTTTTaggttttggattcat | 64 |
| VEGF | TCP | tggtgaggtttgatccgcaTTTTTaggttttggattcat | 65 |
| VEGF | TCP | atctctcctatgtgctggcctTTTTTaggttttggattcat | 66 |
| VEGF | TCP | atctttctttggtctgcattcacTTTTTaggttttggattcat | 67 |
| VEGF | TCP | ccctttccctttcctcgaaTTTTTaggttttggattcat | 68 |
| VEGF | TCP | ccaggacttataccgggatttcTTTTTaggttttggattcat | 69 |
| VEGF | SCP (CP21) | TTTTTTTTATGAATCCAAAACCT | 70 |

Example 2

Capture of Long Nucleic Acids

The techniques described above have been employed to capture exemplary human genomic DNA fragments of at least 35 kilobases in length.

Figure 7A:
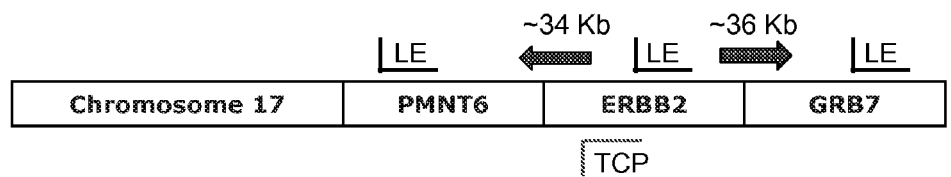
FIG. 7 Panel A schematically depicts the relative locations of ERBB2, GRB7, and PNMT6 on human chromosome 17. Panel B depicts a graph illustrating detection of ERBB2, GRB7, and PNMT6 following capture of DNA fragments with target capture probes against ERBB2.
Figure 7B:
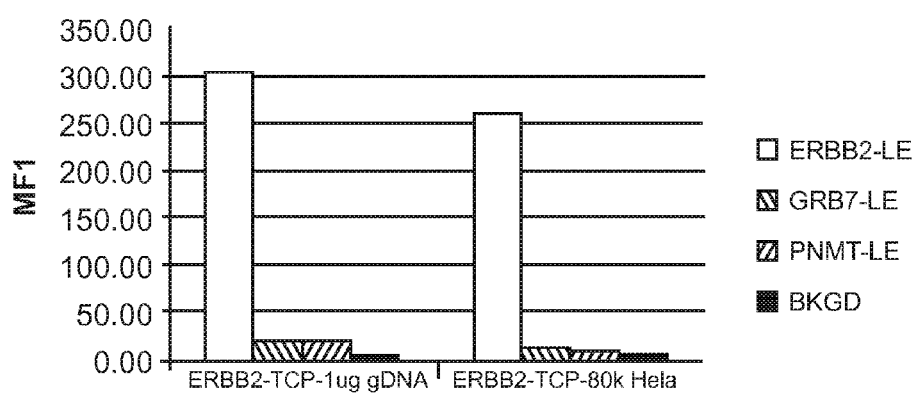

PNMT6 and GRB7 flank ERBB2 on chromosome 17, with PNMT6 being about 34 kb upstream of ERBB2 and GRB7 about 36 kb downstream (FIG. 7 Panel A). Target capture probes complementary to, and clustered within a 500 nucleotide region of, ERBB2 were designed. Detection probes (specifically, label extenders (LE) for use in a branched DNA assay) complementary to ERBB2, PNMT6, and GRB7 were also designed. Probe sequences are listed in Table 4 below.

Branched DNA assays employing the probes were performed in parallel. DNA fragments were captured from two samples, human normal fetal brain genomic DNA (1 µg) and a HeLa cell lysate (from 80,000 cells). Samples were gently lysed, processed without any sonication, and carefully handled to minimize DNA shearing and preserve the length of the resulting DNA fragments. DNA was diluted to the desired concentration with nuclease-free water. DNA was denatured together with the ERBB2 target capture probes and either the PNMT6, GRB7, or ERBB2 label extenders by adding 2.5M NaOH and 20 mM EDTA and incubating at 55° C. for 30 minutes, followed by neutralization of the NaOH by adding 2M HEPES. The DNA/probe mixture was heat-denatured at 95° C. for 5 minutes, cooled down, and kept at 54° C. The denatured DNA/probe mixture was added to beads bearing a support capture probe complementary to the ERBB2 capture probes and hybridized overnight. Detection was performed by hybridizing a pre-amplifier, amplifier, and label probe to the label extenders and then detecting signal from the label probe basically as described in the Quanti-Gene® Plex 2.0 Assay User Manual (Affymetrix, Inc.).

As shown in FIG. 7 Panel B and Table 3, capturing genomic DNA fragments with ERBB2 target capture probes and detecting with ERBB2 label extenders results in a strong signal. Capturing genomic DNA fragments with ERBB2 target capture probes and detecting with PNMT6 or GRB7 label extenders also produces a signal above background. Since the distance between the GRB7 label extenders and the ERBB2 target capture probes is approximately 36 kb and the distance between the PNMT6 label extenders and the ERBB2 target capture probes is approximately 34 kb, these signals indicate that DNA fragments of at least about 35 kb were captured.

TABLE 3

Signal observed using target capture probes to ERBB2 with label extenders to different genes.

| | ERBB2-TCP 1 µg gDNA | ERBB2-TCP 80k HeLa |
|---|---|---|
| ERBB2-LE | 305.67 | 261.70 |
| GRB7-LE | 21.33 | 12.70 |
| PNMT-LE | 19.50 | 9.70 |
| Background | 4 | 4.30 |

TABLE 4

Support capture probe (SCP), target capture probe (TCP), label extender (LE), and blocking probe (BL, hybridize to regions of the target not occupied by the target capture probes or label extenders) sequences for the assay illustrating capture of long DNA fragments.

| Gene Name | Probe Type | Sequence | SEQ ID NO |
|---|---|---|---|
|  | SCP | TTTTTTTTatctgctattaatcc | 71 |
| ERBB2 | TCP | tgtgacattatgggtctgggagaTTTTTggattaatagcagat | 72 |
| ERBB2 | TCP | cccagtgtcacttgaatgggcTTTTTggattaatagcagat | 73 |
| ERBB2 | TCP | ctgcagggcatagagatgaatcTTTTTggattaatagcagat | 74 |
| ERBB2 | TCP | ctcgtcatgtttacagatggctgTTTTTggattaatagcagat | 75 |
| ERBB2 | TCP | catcttatgtttggccacccaTTTTTggattaatagcagat | 76 |
| ERBB2 | TCP | gaagcccctctagagtgacatctcTTTTTggattaatagcagat | 77 |
| ERBB2 | BL | gctgagctttggggacacag | 78 |
| ERBB2 | BL | ggcccaggccctggtc | 79 |
| ERBB2 | BL | agggttctcaactaaagaccctg | 80 |
| ERBB2 | BL | tcactcagtgagcagctgagct | 81 |
| ERBB2 | BL | catgtacctcctctgagggagtaag | 82 |
| ERBB2 | BL | cgcaattcattacctcatttaactct | 83 |
| ERBB2 | BL | tcctcccctgggaagaga | 84 |
| ERBB2 | LE | caagggaagtattggcttttctgTTTTTgtacttatcatgac | 85 |
| ERBB2 | LE | gtcattttactgtagtattcatggaaacTTTTTatttgtctcaccca | 86 |
| ERBB2 | LE | ggtgtttgtggtcggggaatTTTTTgtacttatcatgac | 87 |
| ERBB2 | LE | tgatgtcaggcctgatacaccaTTTTTatttgtctcacacc | 88 |
| ERBB2 | LE | ggtctgggaacttgctcaagaTTTTTgtacttatcatgac | 89 |
| ERBB2 | LE | cgatttagcttctgccctggaTTTTTatttgtctcacacc | 90 |
| ERBB2 | LE | agtaaatattcaccaagttgcaggtaTTTTTgtacttatcatgac | 91 |
| ERBB2 | LE | agctgttacagccaagtttaggtcTTTTTatttgtctcacacc | 92 |
| ERBB2 | LE | tgtcccagttctgtttacaaagcTTTTTgtacttatcatgac | 93 |
| ERBB2 | LE | agaattattctagcgaatgtttgtgtTTTTTatttgtctcacacc | 94 |
| ERBB2 | LE | atgtgtactctttcaaggagtgggTTTTTgtacttatcatgac | 95 |
| ERBB2 | LE | gccgaggtggggtaagggTTTTTatttgtctcacacc | 96 |
| GRB7 | BL | ggggcaccgccggg | 97 |
| GRB7 | BL | cgatgctttgggtgggga | 98 |
| GRB7 | BL | cagggcaggggctctgag | 99 |
| GRB7 | BL | cctgtggtaccctctggc | 100 |
| GRB7 | BL | gcccctccctggcct | 101 |
| GRB7 | BL | cctcctggcaggaccctga | 102 |
| GRB7 | BL | cgaggcaggcgtggcc | 103 |
| GRB7 | LE | tgtcaggaggaacttcatccacaTTTTTgtacttatcatgac | 104 |
| GRB7 | LE | cgggacacccaggagaatgTTTTTatttgtctcacacc | 105 |
| GRB7 | LE | gtgatgggtgtgtcgtgccTTTTTgtacttatcatgac | 106 |

TABLE 4 -continued

Support capture probe (SCP), target capture probe (TCP), label extender (LE), and blocking probe (BL, hybridize to regions of the target not occupied by the target capture probes or label extenders) sequences for the assay illustrating capture of long DNA fragments.

| Gene Name | Probe Type | Sequence | SEQ ID NO |
|---|---|---|---|
| GRB7 | LE | gctggtgtctcttgctagcggTTTTTatttgtctcacacc | 107 |
| GRB7 | LE | ttagactggggtgggagtggTTTTTgtacttatcatgac | 108 |
| GRB7 | LE | ccggggctgtttggaggTTTTTatttgtctcacacc | 109 |
| GRB7 | LE | tcactggggctgtttggagaTTTTTgtacttatcatgac | 110 |
| GRB7 | LE | ccctgcagcctggaatgaagTTTTTatttgtctcacacc | 111 |
| GRB7 | LE | aattctctgctcctctccccaTTTTTgtacttatcatgac | 112 |
| GRB7 | LE | caagcactgccctcccgTTTTTatttgtctcacacc | 113 |
| GRB7 | LE | gatttgaatctacttctaaccccttcTTTTTgtacttatcatgac | 114 |
| GRB7 | LE | tctgaggccaggctctaatgtTTTTTatttgtctcacacc | 115 |
| PNMT | BL | ggagccggggccttc | 116 |
| PNMT | BL | ggcgctggctgcagga | 117 |
| PNMT | BL | ggacgcaccctcatcgacat | 118 |
| PNMT | BL | cctgcccaggtgaagtgtcc | 119 |
| PNMT | BL | ccaggaccctcttcctctgc | 120 |
| PNMT | BL | cctgggctggctggca | 121 |
| PNMT | BL | cgaagggcagcccatgtt | 122 |
| PNMT | LE | cgtagaacagccttgagcccTTTTTgtacttatcatgac | 123 |
| PNMT | LE | ggggcaacagaggcctgagTTTTTatttgtctcacacc | 124 |
| PNMT | LE | ggtgagggttggggaggagTTTTTgtacttatcatgac | 125 |
| PNMT | LE | caaggggtaaggactggggTTTTTatttgtctcacacc | 126 |
| PNMT | LE | atgcctgcctcattgagggTTTTTgtacttatcatgac | 127 |
| PNMT | LE | aactggagcatgtacagccaacTTTTTatttgtctcacacc | 128 |
| PNMT | LE | caaccgccaggagctggTTTTTgtacttatcatgac | 129 |
| PNMT | LE | ccatgacagatttcctggaggtTTTTTatttgtctcacacc | 130 |
| PNMT | LE | tgtaccagctgctcagtgcctTTTTTgtacttatcatgac | 131 |
| PNMT | LE | tggttcaggccccaccgTTTTTatttgtctcacacc | 132 |
| PNMT | LE | ggtaaggaggcaggggctgTTTTTgtacttatcatgac | 133 |
| PNMT | LE | ggagatgcaggggagggaagTTTTTatttgtctcacacc | 134 |
| PNMT | LE | ggggccaatgcttttccaTTTTTgtacttatcatgac | 135 |
| PNMT | LE | ggagctgggttcagtctaactctTTTTTatttgtctcacacc | 136 |

While the foregoing invention has been described in some detail for purposes of clarity and understanding, it will be clear to one skilled in the art from a reading of this disclosure that various changes in form and detail can be made without departing from the true scope of the invention. For example, all the techniques and compositions described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of capturing ten or more different target nucleic acids, the method comprising:

providing a sample comprising or suspected of comprising the ten or more different target nucleic acids (TNA);

providing a solid support having associated therewith a support capture probe (SCP);

providing ten or more subsets of n different target capture probes (TCP), wherein n is at least two, wherein a different subset of target capture probes is provided for each different target nucleic acid, wherein the target capture probes in each subset are capable of hybridizing to nonoverlapping polynucleotide sequences in the corresponding target nucleic acid, and wherein the target capture probes in each subset are capable of hybridizing to the support capture probe;

hybridizing any target nucleic acid present in the sample to its corresponding subset of n target capture probes and hybridizing the subset of n target capture probes to the support capture probe, thereby capturing the target nucleic acid on the solid support in a TNA/TCP/SCP complex, wherein the hybridizing the subset of n target capture probes to the support capture probe is performed at a hybridization temperature which is greater than a melting temperature $T_m$ of a TCP/SCP complex between each individual target capture probe and the support capture probe;

after hybridizing any target nucleic acid present in the sample to its corresponding subset of n target capture probes and hybridizing the subset of n target capture probes to the support capture probe, removing the captured target nucleic acids from the TNA/TCP/SCP complex on the solid support; and after removing the captured target nucleic acids from the solid support, manipulating the captured target nucleic acids;

wherein said manipulating at least comprises sequencing.

2. A method of capturing and sequencing nucleic acids, the method comprising:

providing a sample comprising or suspected of comprising ten or more different target nucleic acids (TNA);

providing a solid support having associated therewith a support capture probe (SCP);

providing ten or more subsets of n different target capture probes (TCP), wherein n is at least two, wherein a different subset of target capture probes is provided for each different target nucleic acid, wherein the target capture probes in each subset are capable of hybridizing to nonoverlapping polynucleotide sequences in the corresponding target nucleic acid, and wherein the target capture probes in each subset are capable of hybridizing to the support capture probe;

hybridizing any target nucleic acid present in the sample to its corresponding subset of n target capture probes and hybridizing the subset of n target capture probes to the support capture probe, thereby capturing the target nucleic acid in a TNA/TCP/SCP complex on the solid support, wherein the hybridizing the subset of n target capture probes to the support capture probe is performed at a hybridization temperature which is greater than a melting temperature $T_m$ of a TCP/SCP complex between each individual target capture probe and the support capture probe;

after hybridizing any target nucleic acid present in the sample to its corresponding subset of n target capture probes and hybridizing the subset of n target capture probes to the support capture probe, removing the captured target nucleic acids from the TNA/TCP/SCP complex on the solid support; and, determining a polynucleotide sequence of one or more of the removed target nucleic acids or a portion thereof.

3. The method of claim 2, wherein removing the target capture probes from the captured target nucleic acids comprises separating the target capture probes and the captured target nucleic acids based on their relative sizes.

4. The method of claim 2, wherein removing the target capture probes from the captured target nucleic acids comprises selectively degrading the target capture probes.

5. The method of claim 2, the target capture probes comprise an affinity tag, and wherein removing the target capture probes from the captured target nucleic acids comprises removing the target capture probes from the captured target nucleic acids by affinity purification.

6. The method of claim 5, wherein the target capture probes comprise a biotin tag, and wherein removing the target capture probes from the captured target nucleic acids by affinity purification comprises removing the target capture probes through binding of the biotin tag to avidin or streptavidin.

7. The method of claim 2, comprising: after capturing the target nucleic acids on the solid support and before determining the polynucleotide sequence of one or more of the captured target nucleic acids or a portion thereof, ligating oligonucleotide adapters to the one or more of the captured target nucleic acids.

8. The method of claim 7, comprising removing the captured target nucleic acids from the solid support prior to ligating the oligonucleotide adapters to the one or more of the captured target nucleic acids.

9. The method of claim 2, wherein determining the polynucleotide sequence comprises determining the polynucleotide sequence by sequencing by synthesis, sequencing by cyclic reversible termination, sequencing by single nucleotide addition, real-time sequencing, dideoxy sequencing, or sequencing by ligation.

10. The method of claim 2, wherein determining the polynucleotide sequence comprises a chromosome walk, resequencing, or sequencing two or more members of a gene or protein family.

11. The method of claim 2, wherein the ten or more target nucleic acids are ten or more fragments of genomic DNA.

12. The method of claim 2, wherein the ten or more different target nucleic acids represent ten or more different exons.

13. The method of claim 2, wherein the ten or more different target nucleic acids are ten or more different RNAs.

14. The method of claim 2, wherein the ten or more target nucleic acids comprise 20 or more, 30 or more, 40 or more, or 50 or more target nucleic acids, and wherein the ten or more subsets of n target capture probes comprise 20 or more, 30 or more, 40 or more, or 50 or more subsets of n target capture probes.

15. The method of claim 2, wherein the solid support comprises particles.

16. The method of claim 2, wherein the solid support comprises particles of a single type, which particles bear the support capture probe.

17. The method of claim 2, wherein the solid support comprises a surface of a well of a multiwell plate.

18. The method of claim 2, wherein the solid support comprises a surface of a well of a multiwell plate, which surface bears the support capture probe.

19. The method of claim 2, wherein n is at least three.

20. The method of claim 2, wherein n is at most ten.

21. The method of claim 2, wherein each target capture probe comprises a polynucleotide sequence U-1 that is complementary to a polynucleotide sequence U-2 in the support capture probe, and wherein U-1 and U-2 are 20 nucleotides or less in length.

22. The method of claim 21, wherein U-1 and U-2 are between 9 and 17 nucleotides in length.

23. The method of claim 2, wherein the hybridization temperature is about 5° C. or more greater than the $T_m$.

24. A method of identifying the presence of one or more target nucleic acids in a sample, the method comprising:

providing a sample comprising or suspected of comprising ten or more different target nucleic acids;

providing a solid support having associated therewith a support capture probe;

providing ten or more subsets of n different target capture probes, wherein n is at least two, wherein a different subset of target capture probes is provided for each different target nucleic acid, wherein the target capture probes in each subset are capable of hybridizing to nonoverlapping polynucleotide sequences in the corresponding target nucleic acid, and wherein the target capture probes in each subset are capable of hybridizing to the support capture probe;

hybridizing any target nucleic acid present in the sample to its corresponding subset of n target capture probes and hybridizing the subset of n target capture probes to the support capture probe, thereby capturing the target nucleic acid in a TNA/TCP/SCP complex on the solid support, wherein the hybridizing the subset of n target capture probes to the support capture probe is performed at a hybridization temperature which is greater than a melting temperature $T_m$ of a TCP/SCP complex between each individual target capture probe and the support capture probe;

after hybridizing any target nucleic acid present in the sample to its corresponding subset of n target capture probes and hybridizing the subset of n target capture probes to the support capture probe, removing the captured target nucleic acids from the TNA/TCP/SCP complex on the solid support; and sequencing the removed target nucleic acids; and identifying the captured target nucleic acids, thereby determining which of the ten or more different target nucleic acids were present in the sample.

25. The method of claim 24, wherein said determining which target nucleic acids were present takes place after removing the captured target nucleic acids from the solid support.

* * * * *

```
                              SEQUENCE LISTING

<160> NUMBER OF SEQ ID NOS: 136

<210> SEQ ID NO 1
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 1
agcagcaggc tctgcagctt tttttgtgca gtgttata                              38

<210> SEQ ID NO 2
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 2
gcgggtgcag agatgctgtt tttttgtgca gtgttata                              38

<210> SEQ ID NO 3
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 3
tacagctcca ggcgggtctt tttttgtgca gtgttata                              38

<210> SEQ ID NO 4
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 4
tgagcttggt gaggctgcct tttttttgtgc agtgttata                            39

<210> SEQ ID NO 5
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 5
tgcttgtagt ggctggccat tttttttgtgc agtgttata                            39

<210> SEQ ID NO 6
<211> LENGTH: 23
<212> TYPE: DNA
<213> ORGANISM: Artificial
<220> FEATURE:
<223> OTHER INFORMATION: synthetic oligonucleotide probe
```

```
<400> SEQUENCE: 6
ttttttttta taacactgca caa                                        23

<210> SEQ ID NO 7
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 7
tgacggtgcc atggaatttt ttttaaaact atacgtgct                       39

<210> SEQ ID NO 8
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 8
agcttcccgt tctcagcctt ttttaaaact atacgtgct                       39

<210> SEQ ID NO 9
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 9
tctcgctcct ggaagatggt tttttaaaac tatacgtgct                      40

<210> SEQ ID NO 10
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 10
gcaaatgagc cccagccttt ttaaaactat acgtgct                         37

<210> SEQ ID NO 11
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 11 cctttggct cccccctttt ttaaaactat acgtgct                          37

<210> SEQ ID NO 12
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 12
catggatgac cttggccagt ttttaaaact atacgtgct                       39

<210> SEQ ID NO 13
<211> LENGTH: 39
```

```
<212> TYPE: DNA
<213> ORGANISM: Artificial
<220> FEATURE:
<223> OTHER INFORMATION: synthetic oligonucleotide probe

<400> SEQUENCE: 13
gctcagggat gaccttgcct ttttaaaact atacgtgct                          39

<210> SEQ ID NO 14
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 14 tttttttag cacgtatagt ttt                                            23

<210> SEQ ID NO 15
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 15
cactctcctc tttccaattc ttcattttt tttcacacac attaac                   46

<210> SEQ ID NO 16
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 16
ttggctctgc attatttttc tgttttttt cacacacatt aac                      43

<210> SEQ ID NO 17
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 17
tctcgtttct ttttgttgct attgttttt tcacacacat taac                     44

<210> SEQ ID NO 18
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 18
atgagttcat gtattgcttt gcgttttttt tcacacacat taac                    44

<210> SEQ ID NO 19
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 19
```

```
ttccctgttt tagctgctgg ttttttttcac acacattaac                    40
```

<210> SEQ ID NO 20
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 20

```
atattcccca tataaataat gttaaatatt ttttttttcac acacattaac          50
```

<210> SEQ ID NO 21
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 21

```
ttttttttgt taatgtgtgt gaa                                       23
```

<210> SEQ ID NO 22
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 22

```
agtgggtgca gctgttctca tttttccgtg cttttctaat                     40
```

<210> SEQ ID NO 23
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 23

```
ctcggagatc tcgaagcatg tttttccgt gcttttctaa t                    41
```

<210> SEQ ID NO 24
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 24

```
gctgatcctt catttgaaag aaattttttcc gtgcttttct aat                43
```

<210> SEQ ID NO 25
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 25

```
ctgggtcttg gttctcagct tttttccgt gcttttctaa t                    41
```

<210> SEQ ID NO 26
<211> LENGTH: 39
<212> TYPE: DNA
<213> ORGANISM: Artificial

```
<220> FEATURE:
<223> OTHER INFORMATION: synthetic oligonucleotide probe

<400> SEQUENCE: 26
gcctcagcct gagggtcttt ttttccgtgc ttttctaat                    39

<210> SEQ ID NO 27
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 27
ccgattttgg agacctctaa tttatttttc cgtgcttttc taat              44

<210> SEQ ID NO 28
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 28 tttttttat tagaaaagca cgg                                      23

<210> SEQ ID NO 29
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 29
gcagaggtcc aggtcctggt ttttaacgtg tattccatt                    39

<210> SEQ ID NO 30
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 30 tgaagcccctt gctgtagtgg tttttttaacg tgtattccat t               41

<210> SEQ ID NO 31
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 31
cctggaaggt ctgtgggcat ttttaacgtg tattccatt                    39

<210> SEQ ID NO 32
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 32
aaagaaggtg ctcaggtcat tcttttttaa cgtgtattcc att               43
```

<210> SEQ ID NO 33
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 33
ggagagcttt cagttcatat ggatttttaa cgtgtattcc att        43

<210> SEQ ID NO 34
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 34
ccatatcctg tccctggagg tttttttaacg tgtattccat t        41

<210> SEQ ID NO 35
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 35
attcttttcc ttgaggccca ttttttaacgt gtattccatt        40

<210> SEQ ID NO 36
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 36
ttttttttaa tggaatacac gtt        23

<210> SEQ ID NO 37
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 37
tgagtttggg attcttgtaa ttattaattt ttgaagttac cgttttc        47

<210> SEQ ID NO 38
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 38
tggccttctt gggcatgtat ttttgaagtt accgttttc        39

<210> SEQ ID NO 39
<211> LENGTH: 44
<212> TYPE: DNA
<213> ORGANISM: Artificial
<220> FEATURE:
<223> OTHER INFORMATION: synthetic oligonucleotide probe

```
<400> SEQUENCE: 39
ctccagaggt tgagttctt cttcttttg aagttaccgt tttc                    44

<210> SEQ ID NO 40
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 40
tcagatccct ttagttccag aactttttg aagttaccgt tttc                   44

<210> SEQ ID NO 41
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 41
aataaataga aggcctgata tgttttattt ttgaagttac cgttttc               47

<210> SEQ ID NO 42
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 42 tttttttga aacggtaac ttc                                           23

<210> SEQ ID NO 43
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 43
gagcttctct ttcgttcccg tttttgggga acatagaaaa                       40

<210> SEQ ID NO 44
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 44
tgtggagaag gagttcatag ctgtttttgg ggaacataga aaa                   43

<210> SEQ ID NO 45
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 45
agccccaggg agaaggcttt ttggggaaca tagaaaa                          37

<210> SEQ ID NO 46
```

<211> LENGTH: 41
<212> TYPE: DNA
<213> ORGANISM: Artificial
<220> FEATURE:
<223> OTHER INFORMATION: synthetic oligonucleotide probe

<400> SEQUENCE: 46
tgtctccttt ctcagggctg attttttgggg aacatagaaa a                41

<210> SEQ ID NO 47
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 47
cctcattgaa tccagattgg aattttggg gaacatagaa aa                42

<210> SEQ ID NO 48
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 48
gaagagccct caggctggat ttttggggaa catagaaaa                   39

<210> SEQ ID NO 49
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 49
tttttttttt ttctatgttc ccc                                    23

<210> SEQ ID NO 50
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 50
tgcacccagt tttccttggt tttttcaaa tgttagcct                    39

<210> SEQ ID NO 51
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 51
ttttatgaat tctcagccct cttttttttt caaatgttag cct              43

<210> SEQ ID NO 52
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 52
cggatattct cttggcccectt ttttttttcaa atgttagcct                 40

<210> SEQ ID NO 53
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 53
tgtggatcct ggctagcaga ttttttttcaa atgttagcct                  40

<210> SEQ ID NO 54
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 54
acccaattgt ttgtttgttt aatcttttttt tcaaatgtta gcct             44

<210> SEQ ID NO 55
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 55 tttttttttag gctaacattt gaa                                    23

<210> SEQ ID NO 56
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 56
cgagaagatg atctgactgc ctgttttttct gagtcaaagc att              43

<210> SEQ ID NO 57
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 57
gctgcccctc agcttgagtt tttctgagtc aaagcatt                     38

<210> SEQ ID NO 58
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 58
gtctggtagg agacggcgat tttttctgag tcaaagcatt                   40

<210> SEQ ID NO 59
<211> LENGTH: 42
<212> TYPE: DNA

```
<213> ORGANISM: Artificial
<220> FEATURE:
<223> OTHER INFORMATION: synthetic oligonucleotide probe

<400> SEQUENCE: 59
tcccagatag atgggctcat acttttttctg agtcaaagca tt                    42

<210> SEQ ID NO 60
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 60
tcgggccgat tgatctcatt tttctgagtc aaagcatt                          38

<210> SEQ ID NO 61
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 61
cccccaattc tcttttttgag cttttttctga gtcaaagcat t                    41

<210> SEQ ID NO 62
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 62 tttttttttaa tgctttgact cag                                         23

<210> SEQ ID NO 63
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 63
aaggctccaa tgcacccatt tttaggtttt ggattcat                          38

<210> SEQ ID NO 64
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 64
ctgccatggg tgcagccttt ttaggttttg gattcat                           37

<210> SEQ ID NO 65
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 65
tggtgaggtt tgatccgcat ttttaggttt tggattcat                         39
```

<210> SEQ ID NO 66
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 66
atctctccta tgtgctggcc ttttttaggt tttggattca t          41

<210> SEQ ID NO 67
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 67
atctttcttt ggtctgcatt cactttttag gttttggatt cat        43

<210> SEQ ID NO 68
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 68
ccctttccct ttcctcgaat ttttaggttt tggattcat            39

<210> SEQ ID NO 69
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 69
ccaggactta taccgggatt tcttttagg ttttggattc at          42

<210> SEQ ID NO 70
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 70 tttttttat gaatccaaaa cct                              23

<210> SEQ ID NO 71
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 71 tttttttat ctgctattaa tcc                              23

<210> SEQ ID NO 72
<211> LENGTH: 43
<212> TYPE: DNA
<213> ORGANISM: Artificial
<220> FEATURE:

<223> OTHER INFORMATION: synthetic oligonucleotide probe

<400> SEQUENCE: 72
tgtgacatta tgggtctggg agatttttgg attaatagca gat         43

<210> SEQ ID NO 73
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 73
cccagtgtca cttgaatggg cttttttggat taatagcaga t         41

<210> SEQ ID NO 74
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 74
ctgcagggca tagagatgaa tcttttttgga ttaatagcag at         42

<210> SEQ ID NO 75
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 75
ctcgtcatgt ttacagatgg ctgttttttgg attaatagca gat         43

<210> SEQ ID NO 76
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 76
catcttatgt ttggccaccc attttttggat taatagcaga t         41

<210> SEQ ID NO 77
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 77
gaagcccctc tagagtgaca tctcttttttg gattaatagc agat         44

<210> SEQ ID NO 78
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 78
gctgagcttt ggggacacag         20

```
<210> SEQ ID NO 79
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 79
ggcccaggcc ctggtc                                                     16

<210> SEQ ID NO 80
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 80
agggttctca actaaagacc ctg                                             23

<210> SEQ ID NO 81
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 81
tcactcagtg agcagctgag ct                                              22

<210> SEQ ID NO 82
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 82
catgtacctc ctctgaggga gtaag                                           25

<210> SEQ ID NO 83
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 83
cgcaattcat tacctcattt aactct                                          26

<210> SEQ ID NO 84
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 84 tcctcccct gggaagaga                                                   19

<210> SEQ ID NO 85
<211> LENGTH: 42
<212> TYPE: DNA
<213> ORGANISM: Artificial
<220> FEATURE:
<223> OTHER INFORMATION: synthetic oligonucleotide probe
```

```
<400> SEQUENCE: 85
caagggaagt attggctttt ctgttttgt acttatcatg ac                              42

<210> SEQ ID NO 86
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 86
gtcattttac tgtagtattc atggaaactt tttatttgtc tcacacc                         47

<210> SEQ ID NO 87
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 87
ggtgtttgtg gtcggggaat tttttgtact tatcatgac                                  39

<210> SEQ ID NO 88
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 88
tgatgtcagg cctgatacac cattttatt tgtctcacac c                                41

<210> SEQ ID NO 89
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 89
ggtctgggaa cttgctcaag atttttgtac ttatcatgac                                 40

<210> SEQ ID NO 90
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 90
cgatttagct tctgccctgg atttttattt gtctcacacc                                 40

<210> SEQ ID NO 91
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 91
agtaaatatt caccaagttg caggtatttt tgtacttatc atgac                           45

<210> SEQ ID NO 92
<211> LENGTH: 43
```

```
<212> TYPE: DNA
<213> ORGANISM: Artificial
<220> FEATURE:
<223> OTHER INFORMATION: synthetic oligonucleotide probe

<400> SEQUENCE: 92
agctgttaca gccaagttta ggtcttttta tttgtctcac acc               43

<210> SEQ ID NO 93
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 93
tgtcccagtt ctgtttacaa agcttttgt acttatcatg ac                42

<210> SEQ ID NO 94
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 94
agaattattc tagcgaatgt ttgtgttttt tatttgtctc acacc              45

<210> SEQ ID NO 95
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 95
atgtgtactc tttcaaggag tgggtttttg tacttatcat gac               43

<210> SEQ ID NO 96
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 96
gccgaggtgg ggtaagggtt tttatttgtc tcacacc                      37

<210> SEQ ID NO 97
<211> LENGTH: 14
<212> TYPE: DNA
<213> ORGANISM: Artificial
<220> FEATURE:
<223> OTHER INFORMATION: synthetic oligonucleotide probe

<400> SEQUENCE: 97
ggggcaccgc cggg                                               14

<210> SEQ ID NO 98
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 98
```

```
cgatgctttg ggtgggga                                          18

<210> SEQ ID NO 99
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 99
cagggcaggg gctctgag                                          18

<210> SEQ ID NO 100
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 100
cctgtggtac ccctctggc                                         19

<210> SEQ ID NO 101
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 101 gcccccteee tggcct                                            16

<210> SEQ ID NO 102
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 102
cctcctggca ggaccctga                                         19

<210> SEQ ID NO 103
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 103
cgaggcaggc gtggcc                                            16

<210> SEQ ID NO 104
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 104
tgtcaggagg aacttcatcc acattttgt acttatcatg ac                42

<210> SEQ ID NO 105
<211> LENGTH: 38
<212> TYPE: DNA
<213> ORGANISM: Artificial
```

<220> FEATURE:
<223> OTHER INFORMATION: synthetic oligonucleotide probe

<400> SEQUENCE: 105
cgggacaccc aggagaatgt ttttatttgt ctcacacc                38

<210> SEQ ID NO 106
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 106
gtgatgggtg tgtcgtgcct ttttgtactt atcatgac                38

<210> SEQ ID NO 107
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 107
gctggtgtct cttgctagcg gtttttattt gtctcacacc              40

<210> SEQ ID NO 108
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 108
ttagactggg gtgggagtgg ttttgtact tatcatgac                39

<210> SEQ ID NO 109
<211> LENGTH: 36
<212> TYPE: DNA
<213> ORGANISM: Artificial
<220> FEATURE:
<223> OTHER INFORMATION: synthetic oligonucleotide probe

<400> SEQUENCE: 109
ccggggctgt ttggaggttt ttatttgtct cacacc                  36

<210> SEQ ID NO 110
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 110
tcactggggc tgtttggaga ttttgtact tatcatgac                39

<210> SEQ ID NO 111
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 111
ccctgcagcc tggaatgaag ttttatttg tctcacacc                39

<210> SEQ ID NO 112
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 112
aattctctgc tcctctcccc attttttgtac ttatcatgac                    40

<210> SEQ ID NO 113
<211> LENGTH: 36
<212> TYPE: DNA
<213> ORGANISM: Artificial
<220> FEATURE:
<223> OTHER INFORMATION: synthetic oligonucleotide probe

<400> SEQUENCE: 113
caagcactgc cctcccgttt ttatttgtct cacacc                         36

<210> SEQ ID NO 114
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 114
gatttgaatc tacttctaac cccttctttt tgtacttatc atgac               45

<210> SEQ ID NO 115
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 115
tctgaggcca ggctctaatg tttttttattt gtctcacacc                    40

<210> SEQ ID NO 116
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 116
ggagccgggg gccttc                                               16

<210> SEQ ID NO 117
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 117
ggcgctggct gcagga                                               16

<210> SEQ ID NO 118
<211> LENGTH: 20
<212> TYPE: DNA
<213> ORGANISM: Artificial
<220> FEATURE:
<223> OTHER INFORMATION: synthetic oligonucleotide probe

```
<400> SEQUENCE: 118
ggacgcaccc tcatcgacat                                              20

<210> SEQ ID NO 119
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 119
cctgcccagg tgaagtgtcc                                              20

<210> SEQ ID NO 120
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 120
ccaggaccct cttcctctgc                                              20

<210> SEQ ID NO 121
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 121
cctgggctgg ctggca                                                  16

<210> SEQ ID NO 122
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 122
cgaagggcag cccatgtt                                                18

<210> SEQ ID NO 123
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 123
cgtagaacag ccttgagccc tttttgtact tatcatgac                         39

<210> SEQ ID NO 124
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 124
ggggcaacag aggcctgagt ttttatttgt ctcacacc                          38

<210> SEQ ID NO 125
```

```
<210> SEQ ID NO 125
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 125
ggtgagggtt ggggaggagt ttttgtactt atcatgac                                    38

<210> SEQ ID NO 126
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 126
caaggggtaa ggactggggt ttttatttgt ctcacacc                                    38

<210> SEQ ID NO 127
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 127
atgcctgcct cattgagggt ttttgtactt atcatgac                                    38

<210> SEQ ID NO 128
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 128
aactggagca tgtacagcca acttttttatt tgtctcacac c                                41

<210> SEQ ID NO 129
<211> LENGTH: 36
<212> TYPE: DNA
<213> ORGANISM: Artificial
<220> FEATURE:
<223> OTHER INFORMATION: synthetic oligonucleotide probe

<400> SEQUENCE: 129
caaccgccag gagctggttt ttgtacttat catgac                                      36

<210> SEQ ID NO 130
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 130
ccatgacaga tttcctggag gttttttatt tgtctcacac c                                41

<210> SEQ ID NO 131
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 131
```

```
tgtaccagct gctcagtgcc tttttttgtac ttatcatgac                              40

<210> SEQ ID NO 132
<211> LENGTH: 36
<212> TYPE: DNA
<213> ORGANISM: Artificial
<220> FEATURE:
<223> OTHER INFORMATION: synthetic oligonucleotide probe

<400> SEQUENCE: 132
tggttcaggc cccaccgttt ttatttgtct cacacc                                   36

<210> SEQ ID NO 133
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 133
ggtaaggagg cagggctgt ttttgtactt atcatgac                                  38

<210> SEQ ID NO 134
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 134
ggagatgcag gggagggaag tttttatttg tctcacacc                                39

<210> SEQ ID NO 135
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 135
ggggccaatg cttttttccat ttttgtactt atcatgac                                38

<210> SEQ ID NO 136
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 136
ggagctgggt tcagtctaac tctttttttat ttgtctcaca cc                           42
```